United States Patent
Inoue et al.

(10) Patent No.: US 9,788,902 B2
(45) Date of Patent: Oct. 17, 2017

(54) SURGICAL INSTRUMENT DEVICE

(71) Applicant: OLYMPUS CORPORATION, Tokyo (JP)

(72) Inventors: Shintaro Inoue, Asaka (JP); Kosuke Kishi, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 802 days.

(21) Appl. No.: 14/049,467

(22) Filed: Oct. 9, 2013

(65) Prior Publication Data

US 2014/0039519 A1 Feb. 6, 2014

Related U.S. Application Data

(63) Continuation of application No. PCT/JP2012/062725, filed on May 11, 2012.

(30) Foreign Application Priority Data

May 12, 2011 (JP) .................................. 2011-107559

(51) Int. Cl.
  *A61B 34/30* (2016.01)
  *A61B 19/00* (2006.01)
  (Continued)

(52) U.S. Cl.
  CPC .......... *A61B 19/2203* (2013.01); *A61B 34/30* (2016.02); *A61B 34/37* (2016.02);
  (Continued)

(58) Field of Classification Search
  CPC ... A61B 34/30; A61B 34/37; A61B 2090/061; A61B 2090/0811; A61B 2090/064; A61B 2017/00477; Y10S 901/08
  See application file for complete search history.

(56) References Cited

U.S. PATENT DOCUMENTS 5,433,215 A * 7/1995 Athanasiou .......... A61B 5/0053
  600/587
5,673,708 A * 10/1997 Athanasiou ............ A61B 5/103
  600/587

(Continued)

FOREIGN PATENT DOCUMENTS

JP   H05-168584 A   7/1993
JP   06-078886 A   3/1994

(Continued)

OTHER PUBLICATIONS

International Search Report dated Jun. 26, 2012 issued in PCT/JP2012/062725.

(Continued)

*Primary Examiner* — Katherine M Shi
*Assistant Examiner* — Michael Mendoza
(74) *Attorney, Agent, or Firm* — Scully, Scott, Murphy & Presser, P.C.

(57) ABSTRACT

A surgical instrument device includes a surgical instrument portion which is used in a surgical operation, a slave arm which holds the surgical instrument, a driving rod which is formed in a shaft shape, of which one end portion in the axial direction is connected to the surgical instrument and the other end portion in the axial direction is supported by the slave arm, and which transmits a force between the surgical instrument and the slave arm, a distance change detecting unit which detects a change in distance between two points in the axial direction of the driving rod based on a distance when no load is applied to the surgical instrument, and a force calculating unit which calculates a force applied from the surgical instrument or the slave arm to the driving rod based on the change in distance detected by the distance change detecting unit.

7 Claims, 17 Drawing Sheets

(51) Int. Cl.
 *A61B 34/37* (2016.01)
 *A61B 17/00* (2006.01)
 *A61B 90/00* (2016.01)

(52) U.S. Cl.
 CPC .............. *A61B 2017/00477* (2013.01); *A61B 2090/061* (2016.02); *A61B 2090/064* (2016.02); *A61B 2090/0811* (2016.02); *Y10S 901/08* (2013.01)

(56) References Cited

U.S. PATENT DOCUMENTS

| 2009/0024142 A1 | 1/2009 | Morales |
| 2010/0245846 A1 | 9/2010 | Yasuda et al. |
| 2010/0256558 A1 | 10/2010 | Olson et al. |

FOREIGN PATENT DOCUMENTS

| JP | 07-34305 A | 6/1995 |
| JP | 2002-059380 A | 2/2002 |
| JP | 2003-024336 A | 1/2003 |
| JP | 2005-103056 A | 4/2005 |
| JP | 3727937 B2 | 12/2005 |
| JP | 2008-259607 A | 10/2008 |
| JP | 2008-543590 A | 12/2008 |
| JP | 2009-052912 A | 3/2009 |
| JP | 2009-522017 A | 6/2009 |
| JP | 2009-525098 A | 7/2009 |
| JP | 2010-220769 A | 10/2010 |
| JP | 2011-147501 A | 8/2011 |
| JP | 2011-230278 A | 11/2011 |
| JP | 2013-517065 A | 5/2013 |
| WO | 2006/136827 A1 | 12/2006 |
| WO | 2007/088208 A1 | 8/2007 |
| WO | WO 2007/120329 A2 | 10/2007 |
| WO | 2008/042423 A2 | 4/2008 |
| WO | 2008/103797 A2 | 8/2008 |
| WO | 2011/088357 A1 | 7/2011 |

OTHER PUBLICATIONS

Japanese Office Action dated Apr. 1, 2015 from related Japanese Application No. 2011-107559, together with an English language translation.

Extended Supplementary European Search Report dated Oct. 10, 2014 from related European Application 12 78 1664.3.

* cited by examiner

SURGICAL INSTRUMENT DEVICE

This application is a continuation application based on PCT Patent Application No. PCT/JP2012/062725, filed on May 11, 2012, claiming priority based on Japanese Patent Application No. 2011-107559, filed May 12, 2011, the contents of which are incorporated herein by reference.

BACKGROUND OF THE INVENTION

Field of the Invention

The present invention relates to a surgical instrument device. More particularly, the present invention relates to, for example, a surgical instrument device which detects a force applied from a surgical instrument portion provided in a distal end and is appropriately used in a master/slave type manipulator.

Description of Related Art

Hitherto, as a surgical operation assisting system, there is a known master/slave type manipulator which transmits the motion of a master portion manipulated by an operator to a surgical instrument device provided in a slave portion.

In such a manipulator, it is desirable that the manipulation in the master portion be accurately transmitted to the surgical instrument device. Also, it is desirable that the operator manipulates the master portion while accurately recognizing the magnitude of a force acting on a surgical instrument portion of the surgical instrument device with the surgical operation.

For this reason, for example, Japanese Unexamined Patent Application, First Publication No. 2005-103056 discloses a force sense detecting device which detects a force applied to an operation portion (surgical instrument portion) provided in a distal end of an arm portion of a manipulator. The force sense detecting device is provided with an inner pipe which accommodates a driving force transmitting mechanism for transmitting a driving force and a force sense detecting portion to which the deformation of the inner pipe is transmitted. The force sense detecting portion detects a strain amount using a strain gauge which is attached to the outer peripheral wall of the inner pipe through a fixing portion and an engaging portion and detects a deformation amount of a connection portion. The force sense detecting device may detect a force applied to the operation portion based on the strain amount.

SUMMARY OF THE INVENTION

According to a first aspect of the present invention, a surgical instrument device includes a surgical instrument portion which is used in a surgical operation; a surgical instrument device body which holds the surgical instrument portion; a force transmitting member which is formed in a shaft shape, of which one end portion in an axial direction is connected to the surgical instrument portion and the other end portion in the axial direction is supported by the surgical instrument device body, and which transmits a force between the surgical instrument portion and the surgical instrument device body; a distance change detecting unit which detects a change in distance between two points away from each other in the axial direction on the force transmitting member based on a distance when no load is applied to the surgical instrument portion; and a force calculating unit which calculates a force applied from the surgical instrument portion or the surgical instrument device body to the force transmitting member based on the change in distance detected by the distance change detecting unit.

Further, according to a second aspect of the present invention, in the surgical instrument device according to the first aspect of the present invention, the force calculating unit may include a storage unit which stores a conversion equation for converting the change in distance into the force and performs a calculation for converting the change in distance into the force using the conversion equation.

Further, according to a third aspect of the present invention, in the surgical instrument device according to the first aspect or the second aspect of the present invention, the distance change detecting unit may include a first displacement detecting unit which detects a displacement of a distal end side point of the two points away from each other in the axial direction on the force transmitting member and a second displacement detecting unit which detects a displacement of a proximal end side point of the two points away from each other in the axial direction on the force transmitting member. Then, the distance change detecting unit may convert the displacement of the distal end side point detected by the first displacement detecting unit and the displacement of the proximal end side point detected by the second displacement detecting unit into the displacements based on a position where no load is applied to the surgical instrument portion, and calculates the change in distance by a difference between the displacement of the distal end side point and the displacement of the proximal end side point after the conversion.

Further, according to a fourth aspect of the present invention, in the surgical instrument device according to the third aspect of the present invention including the first displacement detecting unit and the second displacement detecting unit, at least one of the first displacement detecting unit and the second displacement detecting unit may be configured of a linear encoder.

Further, according to a fifth aspect of the present invention, in the surgical instrument device according to the third aspect or the fourth aspect of the present invention, the surgical instrument device body may include a driving unit which advances and retracts the proximal end portion of the force transmitting member in the axial direction, and the force transmitting member may be supported by the surgical instrument device body through the driving unit.

Further, according to a sixth aspect of the present invention, in the surgical instrument device according to the fifth aspect of the present invention, the driving unit may include a driving amount detector which detects a driving amount of an advance and retract driving, and the second displacement detecting unit may detect the displacement of the proximal end side point based on the output of the driving amount detector.

Further, according to a seventh aspect of the present invention, in the surgical instrument device according to any one of the third aspect to the sixth aspect of the present invention, the surgical instrument portion may be attachable to and detachable from the surgical instrument device body. The force transmitting member may include a distal end side force transmitting member which is provided in the surgical instrument portion and has a first connection portion provided at the proximal end side thereof and a proximal end side force transmitting member which is provided in the surgical instrument device body and has a second connection portion provided at the distal end side so as to be connected to the first connection portion of the distal end side force transmitting member.

Further, according to an eighth aspect of the present invention, in the surgical instrument device according to the seventh aspect of the present invention which includes the first displacement detecting unit and the second displacement detecting unit and includes the distal end side force transmitting member and the proximal end side force transmitting member, the first displacement detecting unit may detect a displacement of a point on the distal end side force transmitting member, and the second displacement detecting unit may detect the displacement of a point on the proximal end side force transmitting member.

Further, according to a ninth aspect of the present invention, in the surgical instrument device according to the first aspect or the second aspect of the present invention, the distance change detecting unit may include a displacement detecting unit which detects the displacement of one of the two points away from each other in the axial direction on the force transmitting member and a displacement detecting unit holding member which is fixed to the other point of the two points away from each other in the axial direction on the force transmitting member, extends in the axial direction of the force transmitting member, and holds the displacement detecting unit at a predetermined distance from the other point.

Further, according to a tenth aspect of the present invention, in the surgical instrument device according to the ninth aspect of the present invention which includes the displacement detecting unit, the displacement detecting unit may be configured of a linear encoder.

Further, according to an eleventh aspect of the present invention, in the surgical instrument device according to the ninth aspect or the tenth aspect of the present invention, the surgical instrument device body may include a driving unit which advances and retracts the proximal end portion of the force transmitting member in the axial direction, and the force transmitting member may be supported by the surgical instrument device body through the driving unit.

Further, according to a twelfth aspect of the present invention, in the surgical instrument device according to any one of the ninth aspect to the eleventh aspect of the present invention, the surgical instrument portion may be attachable to and detachable from the surgical instrument device body. The force transmitting member may include a distal end side force transmitting member which is provided in the surgical instrument portion and has a first connection portion provided in the proximal end side thereof and a proximal end side force transmitting member which is provided in the surgical instrument device body and has a second connection portion provided at the distal end side thereof so as to be connected to the first connection portion of the distal end side force transmitting member.

Further, according to a thirteenth aspect of the present invention, in the surgical instrument device according to any one of the first aspect to the twelfth aspect of the present invention, the force transmitting member may include a distance change amplifying portion which is provided in a portion between the two points away from each other in the axial direction so that the deformation in the axial direction caused by a force applied from the surgical instrument portion or the surgical instrument device body becomes larger than that of the other portion between the two points.

DETAILED DESCRIPTION OF THE INVENTION

Figure 1:
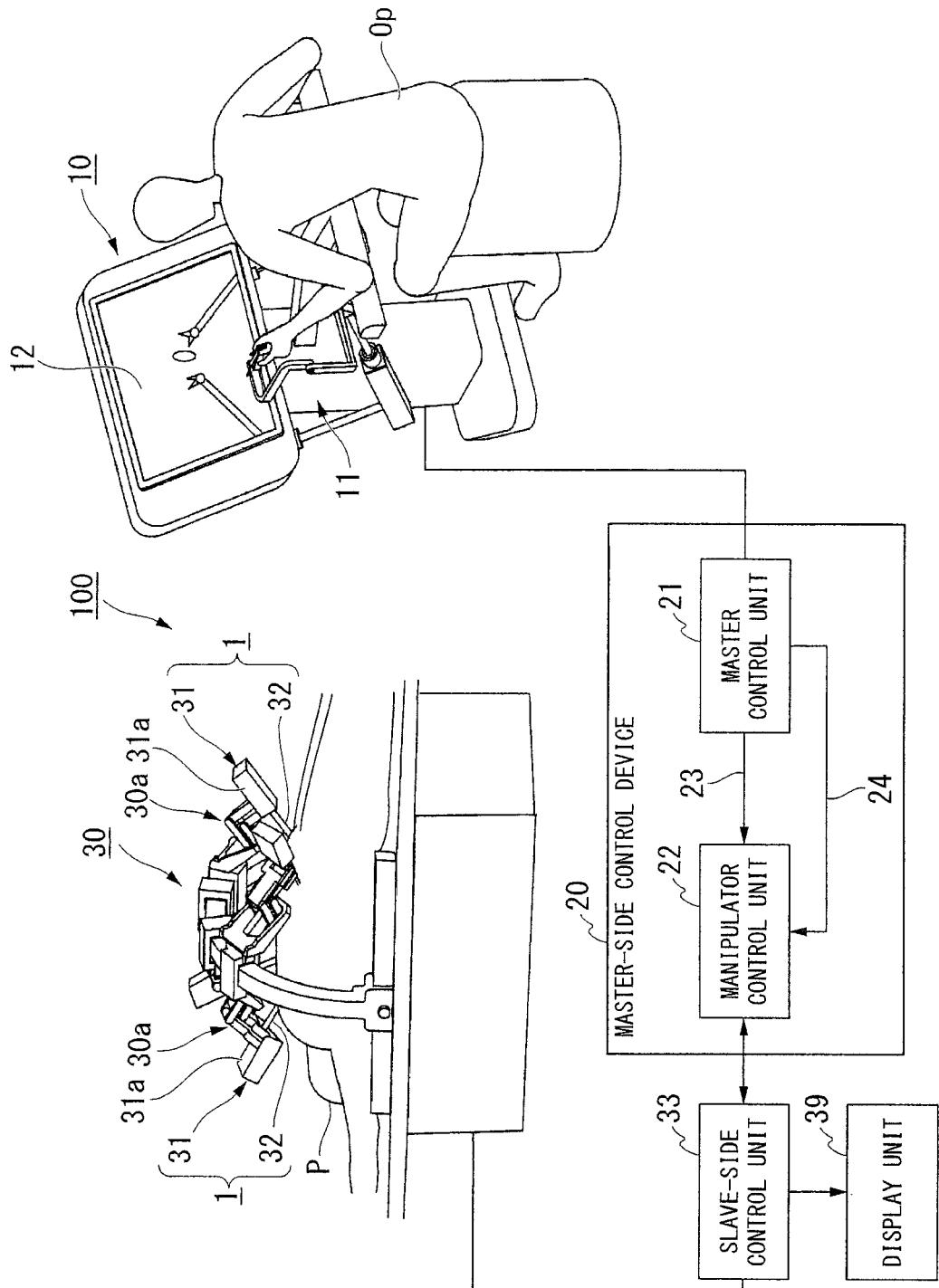
FIG. 1 is a system configuration diagram of a surgical operation assisting system which uses a surgical instrument device according to a first embodiment of the present invention.

Hereinafter, embodiments of the present invention will be described by referring to the accompanying drawings. In all drawings, even of different embodiments, the same reference numerals will be given to the same or equivalent members, and repetitive descriptions thereof will not be repeated.

[First Embodiment]

A surgical instrument device according to a first embodiment of the present invention will be described.

Figure 2A:
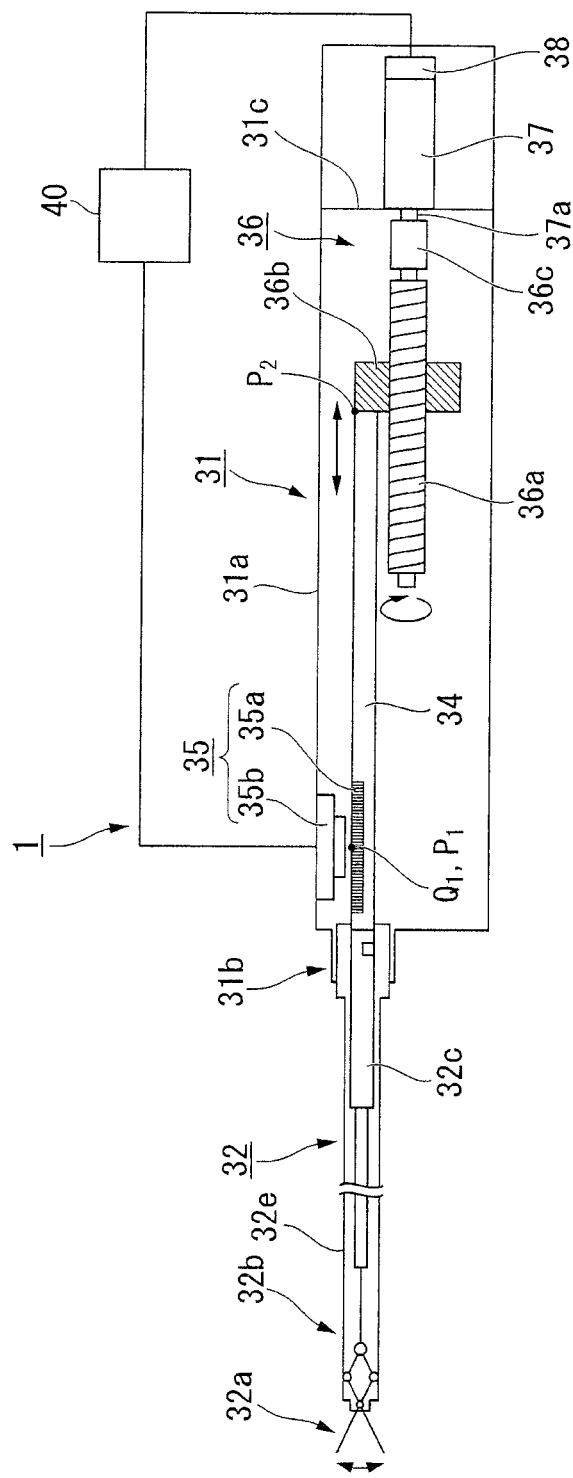
FIG. 2A is a schematic cross-sectional view illustrating a configuration when a surgical instrument portion of the surgical instrument device according to the first embodiment of the present invention is attached.
Figure 2B:
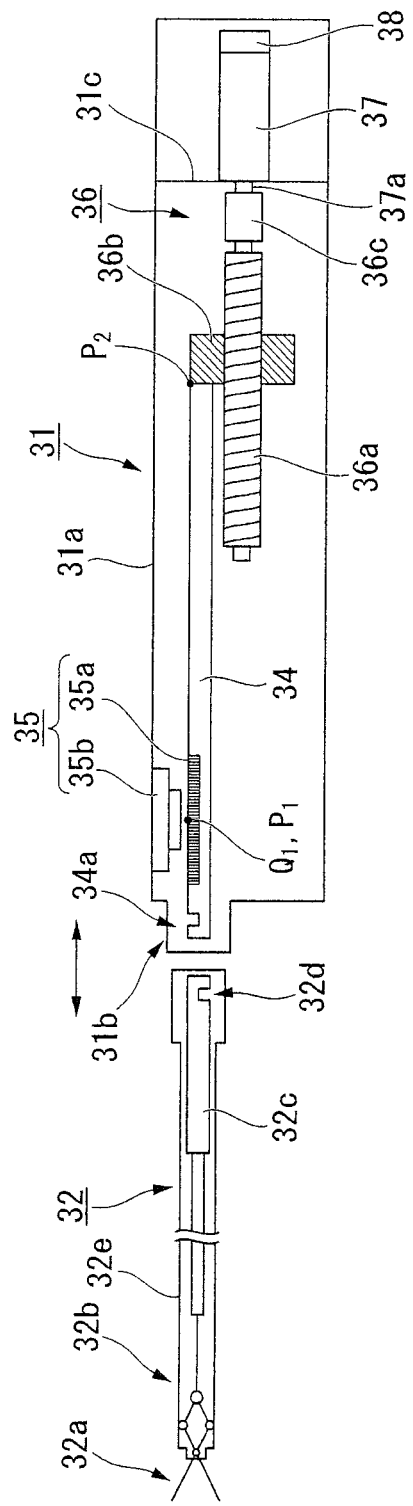
FIG. 2B is a schematic cross-sectional view illustrating a configuration when the surgical instrument portion of the surgical instrument device according to the first embodiment of the present invention is detached.
Figure 3:
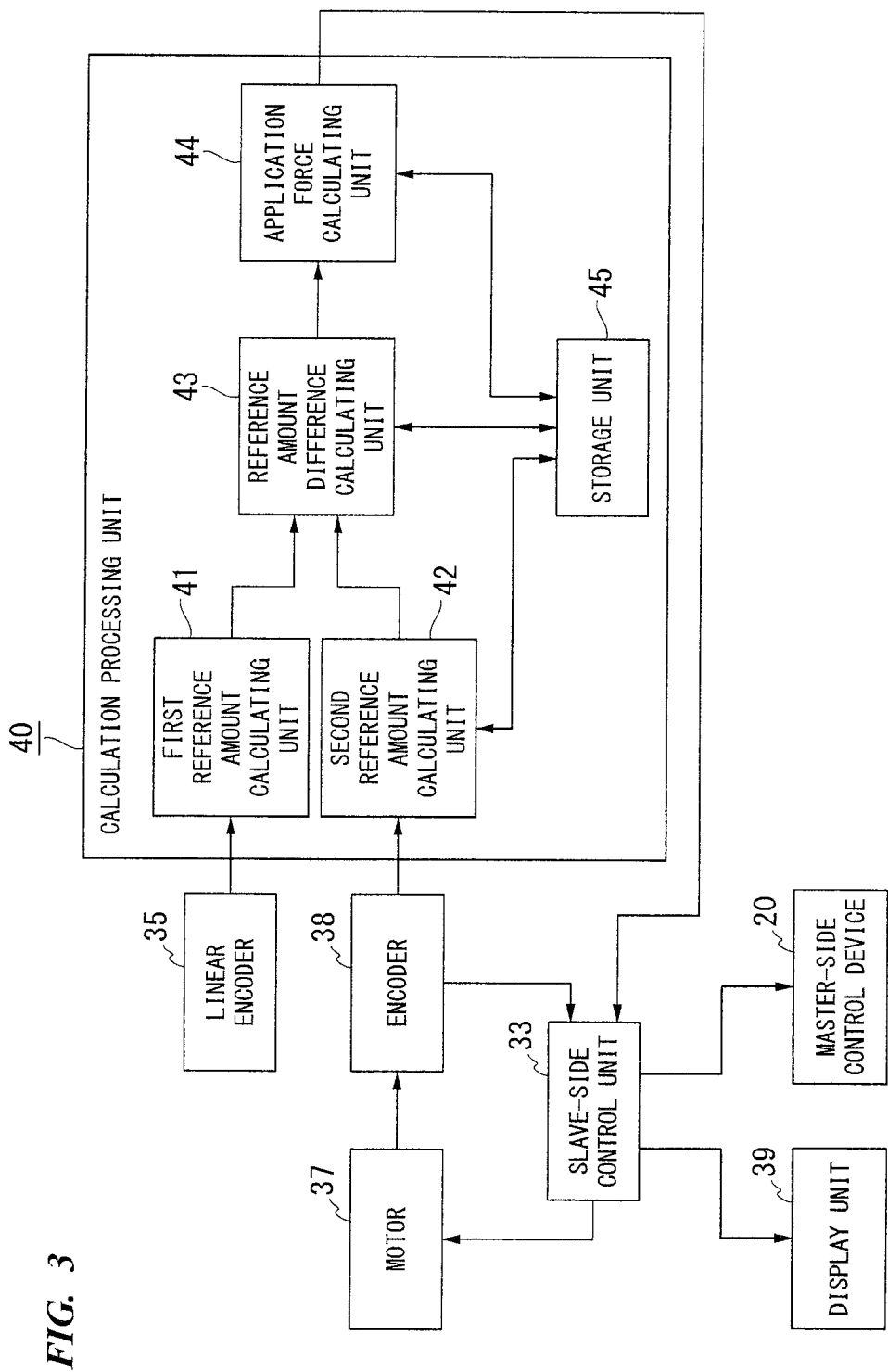
FIG. 3 is a functional block diagram illustrating a functional configuration of a calculation processing unit of the surgical instrument device according to the first embodiment of the present invention.

FIG. 1 is a system configuration diagram of a surgical operation assisting system which uses a surgical instrument device according to a first embodiment of the present invention. FIGS. 2A and 2B are schematic cross-sectional views illustrating a configuration when a surgical instrument portion of the surgical instrument device according to the first embodiment of the present invention is attached and detached. FIG. 3 is a functional block diagram illustrating a functional configuration of a calculation processing unit of the surgical instrument device according to the first embodiment of the present invention.

As shown in FIG. 1, a surgical instrument device 1 of the embodiment corresponds to a device which is appropriately used in a master/slave type surgical operation assisting system 100.

The surgical operation assisting system 100 includes a master manipulation input device 10, a master-side control device 20, a slave-side control unit 33, and a slave manipulator 30.

The master manipulation input device 10 serves as a master which transmits the manipulation motion of the operator $O_p$ to the slave manipulator 30. The master manipulation input device 10 includes a master display unit 12 and a manipulation unit 11.

The master display unit 12 displays images of the treated portion and the vicinity thereof of a patient P captured by a camera (not shown).

The manipulation unit 11 is a member which transmits the manipulation motion of the operator $O_p$ to the slave manipulator 30, and is connected to the master-side control device 20 so that the communication therebetween is enabled. Further, the manipulation unit 11 is disposed in front of the master display unit 12 so that the operator $O_p$ can manipulate the manipulation unit while viewing the master display unit 12.

When the manipulation unit 11 is manipulated by the operator $O_p$, the manipulation unit 11 analyzes the manipulation motion. Then, a manipulation signal for driving the slave manipulator 30 is transmitted to the master-side control device 20.

The master-side control device 20 includes a master control unit 21 and a manipulator control unit 22.

The master control unit 21 receives a manipulation signal transmitted from the master manipulation input device 10, and analyzes a driving amount of a movable portion as a control subject of the slave manipulator 30 for the purpose of realizing the operation based on the manipulation signal. The master control unit 21 transmits a movable portion selection signal 24 and an instruction value 23 to the movable portion selected by the movable portion selection signal 24 to the manipulator control unit 22.

The manipulator control unit 22 controls the operations of the respective movable portions by conducting communication with the movable portion of the slave manipulator 30 selected by the movable portion selection signal 24 through a slave-side control unit 33 for the purpose of realizing the operation of the instruction value 23 transmitted from the master control unit 21.

The slave-side control unit 33 is electrically connected to the manipulator control unit 22 and the respective movable portions of the slave manipulator 30. The slave-side control unit 33 controls the slave manipulator 30 based on a control signal from the manipulator control unit 22, and transmits position information of the respective movable portions, a detection signal necessary for controlling the respective movable portions, and the like transmitted from the slave manipulator 30 to the manipulator control unit 22.

Further, in the embodiment, a display unit 39 is connected to the slave-side control unit 33, so that information of the application force of the surgical instrument portion to be described later is displayed at a position which is seen by the operator $O_p$.

The slave manipulator 30 includes a plurality of the surgical instrument devices 1 and articulated robots 30a which instruct the surgical instrument devices 1 to be movable around the patient P.

The surgical instrument devices 1 and the articulated robots 30a respectively include a plurality of movable portions as control subjects of the slave-side control unit 33. The respective operations of the plurality of movable portions are controlled based on a control signal from the slave-side control unit 33.

As shown in FIGS. 2A and 2B, the surgical instrument device 1 includes a surgical instrument 32 (a surgical instrument portion), a slave arm 31 (a surgical instrument device body), and a calculation processing unit 40.

In the embodiment, the surgical instrument device 1 is formed in a thin and long shaft shape as a whole, and one end side thereof is directed toward the body cavity of the patient P in use. For this reason, hereinafter, in the description of the relative positions of the respective members of the surgical instrument device 1 in the axial direction of the surgical instrument device 1, the side facing the body cavity of the patient P in use will be referred to as a distal end side and the opposite side thereto will be referred to as a proximal end side unless there is a specific indication.

As the surgical instrument 32, a surgical operation tool with an appropriate configuration which is used for various operations inside the body cavity or near the treated portion during the surgical operation may be adopted. Further, the surgical operation tool 32 may include the movable portion or may not include the movable portion. Further, the movable portion may be an operation portion which is operated while directly coming into contact with a diseased portion or other surgical operation tools or may be only a movable mechanism inside the surgical instrument portion. As the specific example of the surgical operation tool 32, a treatment tool such as a needle-holder, scissors, a cautery knife, an ultrasonic treatment tool, forceps, or the like may be given. Hereinafter, as an example, a case of the surgical instrument will be exemplified in which the surgical instrument 32 grips a treated portion or other surgical instrument.

Further, the surgical instrument 32 may be integrated with a slave arm 31, but in the embodiment, the surgical instrument 32 is provided so as to be attachable to and detachable from the slave arm 31. FIG. 2A illustrates a state in which the surgical instrument 32 is attached to the slave arm 31, and FIG. 2B illustrates a state in which the surgical instrument 32 is detached from the slave arm 31.

The surgical instrument 32 includes a gripping portion 32a, a driving link 32b, and a driven portion 32c from the distal end side facing the body cavity of the patient P toward the proximal end side connected to the slave arm 31. Among these components, the driving link 32b and the driven portion 32c are housed inside a cylindrical surgical instrument housing 32e. The gripping portion 32a is, for example, a member which includes gripping arms provided to be openable and closable and grips a gripped subject between the gripping arms when the gripping arms are closed. The driving link 32b is a link mechanism which opens and closes the gripping portion 32a. The driven portion 32c is a bar-like member which advances and retracts the base joint of the driving link 32b in the axial direction of the surgical instrument housing 32e by the driving force which is transmitted from a driving rod 34 inside the slave arm 31 when the surgical instrument 32 is connected to the slave arm 31.

One end of the driven portion 32c is connected to the base joint of the driving link 32b. Further, the other end of the driven portion 32c is provided with a connection portion 32d which is used for the connection to the driving rod 34. Further, the driven portion 32c is formed of, for example, a highly rigid material such as a metal so that the elongation and contraction amount becomes smaller with no buckling even in the event of compression or tension caused by the driving force transmitted from the driving rod 34 to be described later in use.

The slave arm 31 constitutes a surgical instrument device body holding the surgical instrument 32 and includes a cylindrical arm housing 31a. One end side of the arm housing 31a in the axial direction is provided with a fitting portion 31b which is fitted to the proximal end side of the surgical instrument housing 32e of the surgical operation tool 32. Further, as shown in FIG. 1, an outer peripheral portion of the arm housing 31a is connected to the end portion of the articulated robot 30a. For this reason, when the articulated robot 30a is driven, the position and the orientation of the slave arm 31 may be changed according to the degree of freedom of the articulated robot 30a.

In the embodiment, as shown in FIGS. 2A and 2B, the slave arm 31 is provided with the driving rod 34 (force transmitting member), a linear encoder 35 (first displacement detecting unit), a linear driving mechanism 36 (driving unit), a motor 37 (driving unit), and an encoder 38 (second displacement detecting unit).

The driving rod 34 is formed in a shaft shape, and one end portion in the axial direction corresponding to an end portion of the distal end side is provided with a connecting portion 34a which is attachably and detachably connected to the connection portion 32d of the driven portion 32c. Further, the other end portion in the axial direction corresponding to an end portion of the proximal end side is supported by the proximal end side of the slave arm 31 through the linear driving mechanism 36 and the motor 37 which advances and retracts the driving rod 34 in the axial direction. Further, the connecting portion 34a of the driving rod 34 is positioned inside the fitting portion 31b when being attached to and detached from the surgical instrument 32.

Furthermore, the configurations of the connecting portions 34a and 32d are schematically depicted in FIGS. 2A and 2B, and are not particularly limited as long as the driven portion 32c and the driving rod 34 are attachably and detachably connected to each other and are connected with no backlash in the axial direction. For example, the driven portion and the driving rod may be attached to and detached from each other in the axial direction by the concave-convex or may be screw-connected to each other by female and male screws.

Further, in the embodiment, the proximal end portion of the driving rod 34 is connected to a linear driving block 36b of the linear driving mechanism 36 to be described later. As a connection type, for example, various types such as threading, press-inserting, swaging, welding, and screw-connecting using a connecting fitting may be adopted.

In such a connection type, the proximal end portion of the driving rod 34 is restrained by the linear driving block 36b and the like by a certain length. Hereinafter, the proximal end of the driving rod 34 indicates the position closest to the proximal end side at which the driving rod may be elongated and contracted without being restrained by the linear driving block 36b and the like. For example, in the case of FIG. 2A and FIG. 2B, the position closest to the proximal end in the portion at which the driving rod 34 protrudes from the linear driving block 36b is referred to as the proximal end of the driving rod 34, and is indicated by the point $P_2$.

The driving rod 34 is formed of a material which is elastically deformed in at least the axial direction. For example, a metal such as stainless steel may be appropriately adopted. Further, the driving rod 34 is formed in a shape which is not buckled or plastically deformed even in the event of compression or tension which is caused by the reaction from the driven portion 32c or the driving force applied from the linear driving mechanism 36 in use. The elongation and contraction amount in the axial direction may be set to a degree in which a change in the elongation and contraction is measured with high precision at the resolution performance of the linear encoder 35.

Further, in the embodiment, the shape of the cross-section of the driving rod 34 perpendicular to the axis may be formed so as to be uniform except for the connecting portion 34a. For this reason, when a force acts on both end portions of the driving rod 34, the driving rod 34 is uniformly and elastically deformed along the axial direction. As well, the shape of the cross-section perpendicular to the axis is not particularly limited, and may be a circular shape or a polygonal shape. Further, a solid cross-section or a hollow cross-section may be used.

With the above-described configuration, the driving rod 34 serves as a force transmitting member capable of transmitting a force in the axial direction between the surgical instrument 32 and the slave arm 31.

The linear encoder 35 is a first displacement detecting unit which detects the displacement of the distal end side point of two points which are away from each other in the axial direction on the driving rod 34. The linear encoder 35 includes a scale portion 35a which is formed in a pattern for detecting the displacement amount and a detection portion 35b which detects the relative displacement amount with respect to the scale portion 35a by detecting the movement amount of the pattern formed in the scale portion 35a. The linear encoder 35 may be of an incremental type or an absolute value type. In the embodiment, the linear encoder 35 will be described as an incremental type.

Further, as the detection type of the linear encoder 35, there is no particular limitation as long as the linear encoder has resolution performance capable of detecting the displacement of the driving rod 34 with high precision. For example, an optical or magnetic linear encoder may be adopted. In particular, since the optical linear encoder using an LED light source may obtain high resolution performance by miniaturizing the pattern pitch of the scale portion 35a, this is particularly desirable.

The linear encoder 35 of the embodiment is adopted as an optical type. As an example of the appropriate optical linear encoder, for example, a micro linear encoder ML-08/1000 GA (name of product) manufactured by Canon Inc. may be given. In this product, for example, the grating pitch of the scale portion 35a is set to 1.6 µm, and the division number is set to 1000, thereby obtaining the resolution performance of 0.8 nm.

Further, the linear encoder 35 is a member which measures the displacement of the driving rod 34 with respect to the arm housing 31a of the slave arm 31. For this reason, when the scale portion 35a is provided in any one of the driving rod 34 and the arm housing 31a, the detection portion 35b is provided in the other of the driving rod 34 and the arm housing 31a.

In the embodiment, the scale portion 35a is fixed to the side surface of the driving rod 34 corresponding to the vicinity of the proximal end side of the connecting portion 34a. The driving rod 34 moves in conjunction with the driven portion 32c when the driven portion 32c moves in the movable range. For this reason, the scale portion 35a also moves along with the driving rod 34. The length of the scale portion 35a in the axial direction is set to be longer than the maximum movable range of the driven portion 32c connected to the driving rod 34 in use. Further, the detection portion 35b is fixed to a position where the detection portion 35b normally faces the scale portion 35a even when the driven portion 32c moves in the movable range. Further, the detection portion 35b is electrically connected to the calculation processing unit 40, and may transmit a pulse signal according to the displacement of the scale portion 35a to the calculation processing unit 40.

Furthermore, since FIG. 2A is a schematic diagram, it is depicted that the detection portion 35b is connected to the calculation processing unit 40 through the outside of the slave arm 31. However, the interconnection may be provided at the outside or the inside of the slave arm 31.

In the embodiment, a ball screw type linear driving mechanism is adopted as the linear driving mechanism 36. For this reason, the linear driving mechanism 36 includes a ball screw 36a which is formed so as to extend in the axial direction of the arm housing 31a and the linear driving block 36b which is movably guided along the axial direction of the arm housing 31a by a linear driving guide member (not shown) provided inside the slave arm 31 and is screw-connected to the ball screw 36a.

An end portion of the proximal end side of the ball screw 36a is connected to a rotary shaft 37a of the motor 37 through a rotary joint 36c.

Further, an end portion of the proximal end side of the driving rod 34 is connected to the linear driving block 36b. For this reason, when the motor 37 is driven so that the ball screw 36a rotates, the linear driving block 36b advances and retracts by the ball screw 36a, and the driving rod 34 also advances and retracts in the axial direction of the ball screw 36a.

The motor 37 is a member which rotationally drives the ball screw 36a of the linear driving mechanism 36, and is fixed to a fixing member 31c provided inside the proximal end side of the arm housing 31a as shown in FIGS. 2A and 2B. Further, as shown in FIG. 3, the motor 37 is electrically connected to the slave-side control unit 33, and rotates by a rotation angle according to a control signal from the slave-side control unit 33.

Further, the encoder 38 which detects the rotation angle of the rotary shaft 37a is connected to the motor 37. In the embodiment, the rotary shaft 37a and the ball screw 36a are directly connected to each other at the rotary joint 36c. For this reason, the rotation angle detected by the encoder 38 matches the rotation angle of the ball screw 36a.

As shown in FIG. 3, the encoder 38 is electrically connected to the slave-side control unit 33 and the calculation processing unit 40, and transmits information on the rotation angle of the rotary shaft 37a to the slave-side control unit 33 and the calculation processing unit 40. The information on the rotation angle transmitted to the slave-side control unit 33 is fed back to the control of the motor 37 using the slave-side control unit 33.

The rotation angle of the rotary shaft 37a detected by the encoder 38 may be converted into, for example, the movement amount of the linear driving block 36b using the feeding pitch of the ball screw 36a. That is, the encoder 38 constitutes the driving amount detector which detects the advance and retract driving amount. The movement amount of the linear driving block 36b indicates the displacement of the point $P_2$ of the proximal end of the driving rod 34 connected to the linear driving block 36b. Thus, the encoder 38 constitutes a second displacement detecting unit which detects the displacement of the proximal end side point $P_2$ of two points which are away from each other in the axial direction on the driving rod 34.

With the above-described configuration, the linear driving block 36b and the motor 37 constitute a driving unit which advances and retracts the proximal end portion of the driving rod 34 in the axial direction.

In the embodiment, the calculation processing unit 40 is a member which obtains a change in distance in the axial direction between two points (the elongation and contraction amount of the driving rod 34) due to the elastic deformation of the driving rod 34 based on the displacement detected by the linear encoder 35 and the displacement detected by the encoder 38, and obtains a force causing a change in distance by a calculation process, and calculates a change in the distance as a force acting on the driving rod 34. As shown in FIG. 3, the calculation processing unit 40 includes a first reference amount calculating unit 41, a second reference amount calculating unit 42, a reference amount difference calculating unit 43, and an application force calculating unit 44.

The first reference amount calculating unit 41 is electrically connected to the linear encoder 35, detects the displacement of the distal end side point of two points away from each other in the axial direction on the driving rod 34 based on the output of the linear encoder 35, and then transmits the detection result as the displacement $\Delta X_1$ to the reference amount difference calculating unit 43. Furthermore, in the embodiment, as for the positive side and the negative side of the displacement $\Delta X_1$, the direction directed from the proximal end side toward the distal end side is defined as the positive side.

At the time of setting the origin as a start position of the displacement detection, the linear encoder 35 detects the displacement of the point $P_1$ (see FIG. 2A) on the scale portion 35a positioned at the inherent detection position $Q_1$ in the detection portion 35b by reading the passage pattern at the detection position $Q_1$ generated with the movement of the point $P_1$. The detection position $Q_1$ is, for example, the irradiation position of the detection light with respect to the scale portion 35a when the detection portion 35b is an optical type.

For this reason, the scale portion 35a is formed of a material which is sufficiently shorter than the entire length of the driving rod 34 and hardly causes deformation thereof. For this reason, the elongation and contraction of the scale portion 35a may be disregarded. Thus, the linear encoder 35 assumes that the displacement detected by the scale portion 35a is uniform at respective positions on the scale portion 35a. That is, the displacement $\Delta X_1$ detected by the linear encoder 35 is described the displacement of the point $P_1$ detected at the time of setting the origin.

The second reference amount calculating unit 42 is electrically connected to the encoder 38, and transmits the displacement of the proximal end side point of two points away from each other in the axial direction on the driving rod 34 based on the output of the encoder 38 as the displacement $\Delta X_2$ to the reference amount difference calculating unit 43.

The encoder 38 outputs the rotation angle of the ball screw 36a. For this reason, for example, the rotation angle may be converted into the screw feeding amount from the magnitude of the lead of the ball screw 36a, thereby calculating the displacement of the linear driving block 36b.

The displacement of the linear driving block 36b is equal to the displacement of the point $P_2$ of the proximal end of the driving rod 34 connected to the linear driving block 36b. For this reason, the second reference amount calculating unit 42 may calculate the displacement of the point $P_2$.

However, there are mechanical errors, which are different in each device, between the rotation angle of the ball screw 36a and the movement amount of the linear driving block 36b. Therefore, in the embodiment, in order to correct such inherent movement errors of the device, instead of the conversion based on the magnitude of the lead of the ball screw 36a, the correspondence relation between the rotation angle of the encoder 38 and the movement position of the point $P_2$ using the ball screw 36a is measured in advance, and the displacement $\Delta X_2$ is calculated based on the correspondence relation.

The reference amount difference calculating unit 43 converts the displacement $\Delta X_1$ of the point $P_1$ transmitted from the first reference amount calculating unit 41 and the displacement $\Delta X_2$ of the point $P_2$ transmitted from the second reference amount calculating unit 42 into the displacements $\Delta X_1'$ and $\Delta X_2'$ based on the positions of the points $P_1$ and $P_2$ when no load is applied to the surgical instrument 32 connected to the slave arm 31, calculates the difference $\Delta L$ by the following equation (1), and then transmits the difference to the application force calculating unit 44.

$$\Delta L = \Delta X_1' - \Delta X_2' \quad (1)$$

When the surgical instrument 32 and the slave arm 31 are connected to each other and a current is supplied to the surgical instrument device 1, the initialization of the surgical instrument device 1 is performed by the slave-side control unit 33. At this time, the origins of the linear encoder 35 and the encoder 38 are reset, and in the following operations, the positions are set to positions of $\Delta X_1 = 0$ and $\Delta X_2 = 0$.

Thus, when no load is applied to the surgical operation tool 32 in an initialization state, these origins are used as the reference of the displacement in a no-load state, so that $\Delta X_1' = \Delta X_1$ and $\Delta X_2' = \Delta X_2$.

However, there are cases in which a load needs to be applied to the surgical instrument 32 in the initialization state. For example, in a case in which the surgical instrument 32 includes the gripping portion 32a, when there is a need to reliably close the gripping portion 32a in the initialization state, a certain degree of load is applied so that the gripping portions 32a come into press-contact with each other. In this case, the origin in the initialization state may not be set to a position in a no-load state.

For this reason, in the embodiment, the driving states of the surgical instrument 32 in an initialization state and a no-load state are determined for each surgical instrument 32, the reference displacements $\Delta X_{01}$ and $\Delta X_{02}$ in a no-load state based on the origin in the initialization state are obtained by the measurement in advance, and then the reference displacements are stored in a storage unit 45. When the reference displacements in the initialization state and the no-load state are equal to each other, $\Delta X_{01} = 0$ and $\Delta X_{02} = 0$. Thus, the reference amount difference calculating unit 43 calculates the displacements $\Delta X_1'$ and $\Delta X_2'$ from the following equations (2) and (3), and applies the displacements to the above-described equation (1).

$$\Delta X_1' = \Delta X_1 - \Delta X_{01} \quad (2)$$

$$\Delta X_2' = \Delta X_2 - \Delta X_{02} \quad (3)$$

The application force calculating unit 44 calculates the force F applied from the slave arm 31 to the driving rod 34 through the surgical instrument 32 or the linear driving block 36b from the difference $\Delta L$ transmitted from the reference amount difference calculating unit 43. In the embodiment, the driving rod 34 is formed so that the shape of the cross-section perpendicular to the axis between the points $P_1$ and $P_2$ is uniform. For this reason, the application force calculating unit 44 calculates the force F by calculating the following equation (4) based on Hooke's law.

$$F = E \cdot S \cdot (\Delta L / L) \quad (4)$$

Here, E indicates the longitudinal elastic modulus (Young's modulus) of the driving rod 34, S indicates the cross-sectional area of the cross-section perpendicular to the axis between the points $P_1$ and $P_2$ of the driving rod 34, and L indicates the distance in a no-load state between the points $P_1$ and $P_2$ of the driving rod 34. The above-described equation (2) is a conversion equation for converting the difference $\Delta L$ into the force F using the conversion constant $(E \cdot S / L)$.

The storage unit 45 is electrically connected to the second reference amount calculating unit 42, the reference amount difference calculating unit 43, and the application force calculating unit 44, and stores data necessary for the calculation process executed by the calculation processing unit 40. As the data stored in the storage unit 45, as described above, for example, data representing the correspondence relation between the rotation angle of the encoder 38 and the movement position of the point $P_2$ using the ball screw 36a, the reference displacements $\Delta X_{01}$ and $\Delta X_{02}$ in a no-load state, the conversion constant $(E \cdot S / L)$, and the like may be given.

In this way, the storage unit 45 of the embodiment stores the conversion equation for converting a change in distance into a force by storing the conversion constant. Furthermore, as the means for storing the conversion equation, the conversion equation may be stored in the form of a relational equation, a function, a sub-program, a table, and the like. Further, the general conversion equation and the parameter set in the conversion equation may be stored.

The calculation processing unit 40 may be configured of only hardware corresponding to the above-described functional configuration, or may be constructed by the hardware and a computer including a CPU, a memory, an input and output interface, an external storage device, and the like, and the program corresponding to each of the above-described calculation functions may be executed by the computer.

Further, since FIG. 2A is a schematic diagram, the calculation processing unit 40 is depicted as being positioned at the outside of the slave arm 31, but the arrangement position of the calculation processing unit 40 is not particularly limited. For example, the calculation processing unit 40 may be provided inside the arm housing 31a or may be provided in the outer peripheral surface or the proximal end portion of the arm housing 31a. Further, the calculation processing unit 40 may be provided in the slave-side control unit 33. Further, in FIG. 2B, the calculation processing unit 40 is omitted.

With the above-described configuration, the linear encoder 35, the encoder 38, the first reference amount calculating unit 41, the second reference amount calculating unit 42, and the reference amount difference calculating unit 43 constitute the distance change detecting unit which detects a change in distance $\Delta L$ between two points $P_1$ and $P_2$ away from each other in the axial direction on the driving rod 34 based on the distance L when no load is applied to the surgical instrument 32. Further, the application force calculating unit 44 constitutes the force calculating unit which calculates the force applied from the surgical instrument 32 or the slave arm 31 to the driving rod 34 based on the change in distance $\Delta L$ detected by the distance change detecting unit.

Next, the operation of the surgical instrument device 1 of the embodiment will be described.

First, as shown in FIG. 2B, the surgical instrument device 1 is assembled by connecting the surgical instrument 32 to the slave arm 31. Accordingly, the driven portion 32c and the driving rod 34 are connected to each other at the connecting portions 32d and 34a, and the driving link 32b and the linear driving block 36b are connected to each other through the shaft-like member constituted by the driven portion 32c and the driving rod 34.

Next, when a current is supplied to the surgical operation assisting system 100, the surgical instrument device 1 and the articulated robot 30a are initialized by the slave-side control unit 33. In the surgical instrument device 1, the motor 37 is driven to the predetermined initialization position, and the position of the linear driving block 36b is initialized. In this state, the origins of the linear encoder 35 and the encoder 38 are reset. Further, the articulated robot 30a moves to the predetermined initialization position.

Next, the operator $O_p$ manipulates the manipulation unit 11 while viewing the image of the master display unit 12 of the master manipulation input device 10. The manipulation unit 11 analyzes the manipulation motion performed by the operator $O_p$, and transmits a manipulation signal for driving the slave manipulator 30 to the master-side control device 20.

In the master-side control device 20, the movable portion selection signal 24 and the instruction value 23 for controlling the operations of the respective movable portions of the slave manipulator 30 are transmitted from the master control unit 21 to the manipulator control unit 22 based on a manipulation signal. Based on these operations, a control signal is transmitted from the manipulator control unit 22 to the slave-side control unit 33. For example, a control signal to perform an operation in which the gripping portion 32a of the surgical instrument device 1 is opened, the gripping portion 32a moves to a position where a gripped subject is gripped by the articulated robot 30a, and then the gripping portion 32a is closed so as to grip the gripped subject is transmitted.

Accordingly, the motor 37 of the surgical instrument device 1 is driven, the linear driving block 36b moves toward the distal end side, the driven portion 32c moves toward the distal end side through the driving rod 34, and the gripping portion 32a is opened by the driving link 32b. At the time of gripping the gripped object, the motor 37 is reversely rotated so that the linear driving block 36b moves toward the proximal end side.

Together with such a driving operation, the calculation processing unit 40 sequentially calculates the force acting on the driving rod 34 based on the displacement amounts of the points $P_1$ and $P_2$ on the driving rod 34 acquired by the linear encoder 35 and the encoder 38, and outputs a signal which represents information of the force to the slave-side control unit 33.

That is, when the motor 37 is driven, the output signals of the linear encoder 35 and the encoder 38 are respectively and sequentially input to the first reference amount calculating unit 41 and the second reference amount calculating unit 42. The first reference amount calculating unit 41 and the second reference amount calculating unit 42 transmit the displacement $\Delta X_1$ of the point $P_1$ and the displacement $\Delta X_2$ of the point $P_2$ to the reference amount difference calculating unit 43 based on the output signals. In the reference amount difference calculating unit 43, the displacements $\Delta X_1$ and $\Delta X_2$ are converted into the displacements $\Delta X_1'$ and $\Delta X_2'$ based on the above-described equations (2) and (3), the difference $\Delta L$ is calculated based on the above-described equation (1), and the difference is transmitted to the application force calculating unit 44.

The application force calculating unit 44 calculates the force F based on the above-described equation (4), and transmits the force to the slave-side control unit 33. In the embodiment, the force F transmitted to the slave-side control unit 33 is displayed in the form of a numerical value, a graph, or the like on the display unit 39. Accordingly, the operator $O_p$ may recognize the magnitude of the force F acting on the driving rod 34.

The force F which is calculated in this way corresponds to the tension force or the compression force applied to the driving rod 34 at the positions of the points $P_1$ and $P_2$. The tension force or the compression force is applied to respective positions on the driven portion 32c and the driving rod 34 which are integrated with each other by the connecting portions 34a and 32c. Especially, in the case of the embodiment, the tension force acting on the driving rod 34 corresponds to the application force which closes the gripping portion 32a by pulling the driving link 32b toward the proximal end side. The magnitude of the force F corresponds to the pressure which is applied from the gripping portion 32a to the gripped object. For this reason, the operator $O_p$ may adjust the manipulation so that the pressure on the gripped subject becomes appropriate by viewing the display of the magnitude of the force F.

In the embodiment, the force acting on the driving rod 34 is obtained by detecting a change in distance between two points $P_1$ and $P_2$ away from each other on the driving rod 34. For this reason, even in the case of the surgical instrument 32 in which the elongation and contraction amount of the driving rod 34 becomes minute, it is possible to highly precisely detect the elongation and contraction amount of the driving rod 34 by setting a distance L between two points $P_1$ and $P_2$ in a no-load state largely. For example, when the driving rod 34 is formed as a column with a diameter of 1 mm from stainless steel and L=10 (mm), E=193 (GPa), and $S=\pi \times 0.5^2$ (mm$^2$). Thus, when the resolution performance of the linear encoder 35 is set to 0.8 nm, the detection resolution performance of the force F becomes F=0.012(N) based on the above-described equation (4).

In the case of the embodiment, since the average strain is measured by a change in distance between two points, it is possible to reduce the measurement error caused by the local strain distribution by setting a distance between the two points long. For this reason, the highly precise detection may be performed compared to the measurement of the strain gauge. Furthermore, in the case of the embodiment, since the measurement result is output as a pulsed digital signal using the encoder, it is possible to obtain a stable output which is hardly affected by noise.

[First Modified Example]

Next, a modified example of the embodiment (first modified example) will be described.

Figure 4:
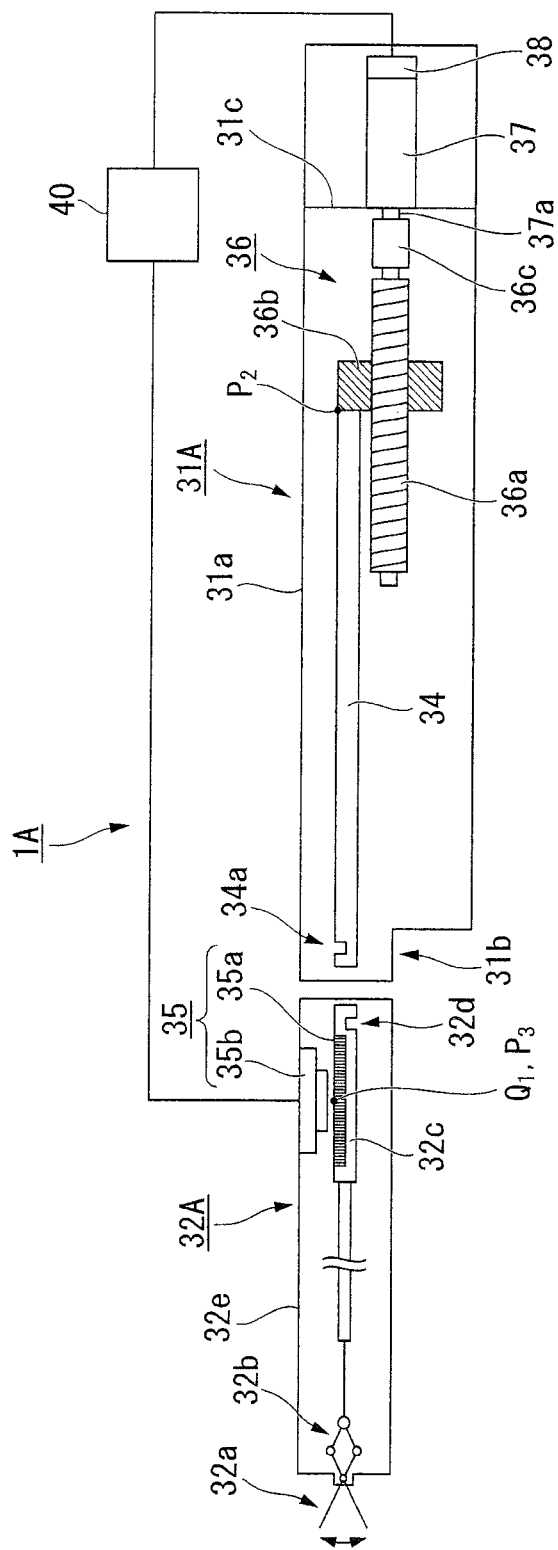
FIG. 4 is a schematic cross-sectional view illustrating a configuration when a surgical instrument portion of a surgical instrument device according to a modified example of the first embodiment of the present invention (first modified example) is detached.

FIG. 4 is a schematic cross-sectional view illustrating a configuration when a surgical instrument portion of a surgical instrument device according to a modified example of the first embodiment of the present invention (first modified example) is detached.

As shown in FIG. 4, a surgical instrument device 1A of the modified example includes a surgical instrument 32A (surgical instrument portion) instead of the surgical instrument 32 of the surgical instrument device 1 of the first embodiment. Furthermore, the surgical instrument device 1A of the modified example does not include the linear encoder 35 which is provided inside the slave arm 31 of the first embodiment. Further, the surgical instrument device 1A may be applied to a surgical operation assisting system 100 instead of the surgical instrument device 1 of the first embodiment. Hereinafter, differences from the first embodiment will be mainly described.

In the surgical instrument 32A, the scale portion 35a is fixed to the side surface near the connection portion 32d of the driven portion 32c. Further, the detection portion 35b is fixed to a position facing the scale portion 35a in the inner peripheral surface of the surgical instrument housing 32e. The fixing position of the detection portion 35b corresponds to a position which normally faces the scale portion 35a when the driven portion 32c moves in the movable range. For this reason, the linear encoder 35 can detect the displacement of the point $P_3$ on the scale portion 35a positioned at the detection position $Q_1$ in the driven portion 32c. Accordingly, the displacement of the point $P_3$ as the distal end side may be detected by the linear encoder 35 and the displacement of the point $P_2$ as the proximal end side may be detected by the encoder 38, on the shaft-like member formed by connecting the driven portion 32c and the driving rod 34 to each other. Furthermore, the detection portion 35b may be provided on the driven portion 32c, and the scale portion 35a may be provided on the surgical instrument housing 32e.

As with the first embodiment, the detection portion 35b is electrically connected to the first reference amount calculating unit 41 of the calculation processing unit 40. Since FIG. 4 is a schematic diagram, it is depicted that the detection portion 35b is connected to the calculation processing unit 40 through the outside of the surgical instrument 32, but the interconnection may be provided at the outside or the inside of the surgical instrument 32. When the interconnection is provided at the inside, a connector which is attachable to and detachable from at the same time when attaching and detaching the surgical instrument 32 may be provided in the fitting portion 31b, and the detection portion 35b may be connected to the calculation processing unit 40 through the interconnection which is connected to the connector and is disposed inside the arm housing 31a. Even when the surgical operation tool is attachably and detachably connected by the connector, since the detection signal from the detection portion 35b is a pulse signal and is not an analog signal as in the case of the output of the strain gauge, it is possible to suppress the measurement error caused by a change of contact resistance due to the repeated insertion and extraction.

According to the configuration of the modified example, it is possible to measure a change in distance between two points $P_3$ and $P_2$ on the shaft-like member when the driven portion 32c and the driving rod 34 are connected to each other using the linear encoder 35 and the encoder 38. For this reason, it is possible to calculate the force F acting on the driven portion 32c and the driving rod 34 as with the first embodiment. However, in the modified example, since the displacement of the point $P_3$ is measured instead of the displacement of the point $P_1$, the distance L in a no-load state or the position of the point $P_3$ in a no-load state changes according to the position of the point $P_3$.

According to the modified example, it is possible to set a distance between two points used for the measurement of a change in distance long compared to the first embodiment.

In the modified example, the linear encoder 35 is disposed at a position different from that of the first embodiment, but constitutes the first displacement detecting unit as with the first embodiment.

Further, the driven portion 32c and the driving rod 34 both constitute the force transmitting member. Then, the driven portion 32c is provided in the surgical operation tool 32 attachable to and detachable from the slave arm 31 and constitutes the distal end side force transmitting member which includes the connection portion 32d as the first connection portion at the proximal end side.

Further, the driving rod 34 constitutes the proximal end side force transmitting member which includes the connecting portion 34a as the second connection portion used for the connection to the connection portion 32d at the distal end side. For this reason, the linear encoder 35 detects the displacement on the distal end side force transmitting member, and the encoder 38 detects the displacement on the proximal end side force transmitting member.

[Second Embodiment]

Figure 5:
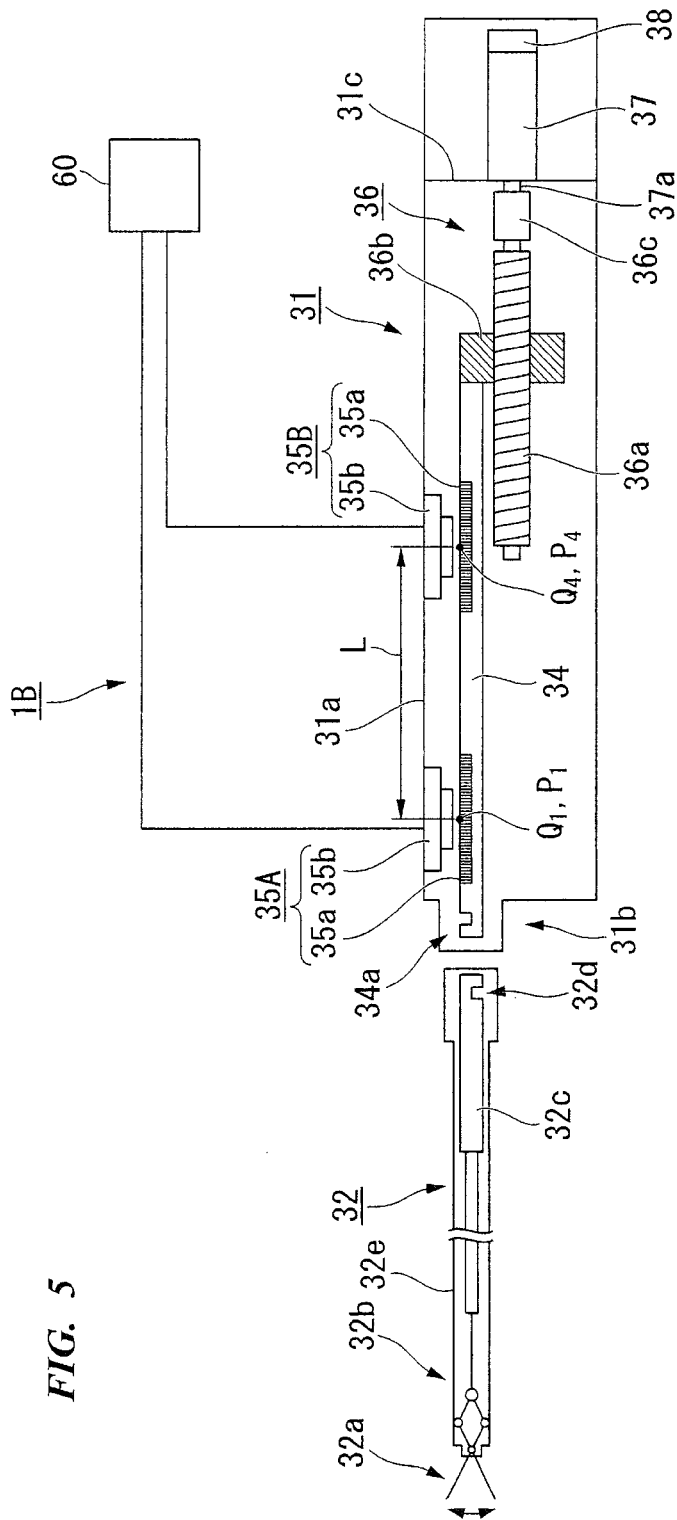
FIG. 5 is a schematic cross-sectional view illustrating a configuration when a surgical instrument portion of a surgical instrument device according to a second embodiment of the present invention is detached.
Figure 6:
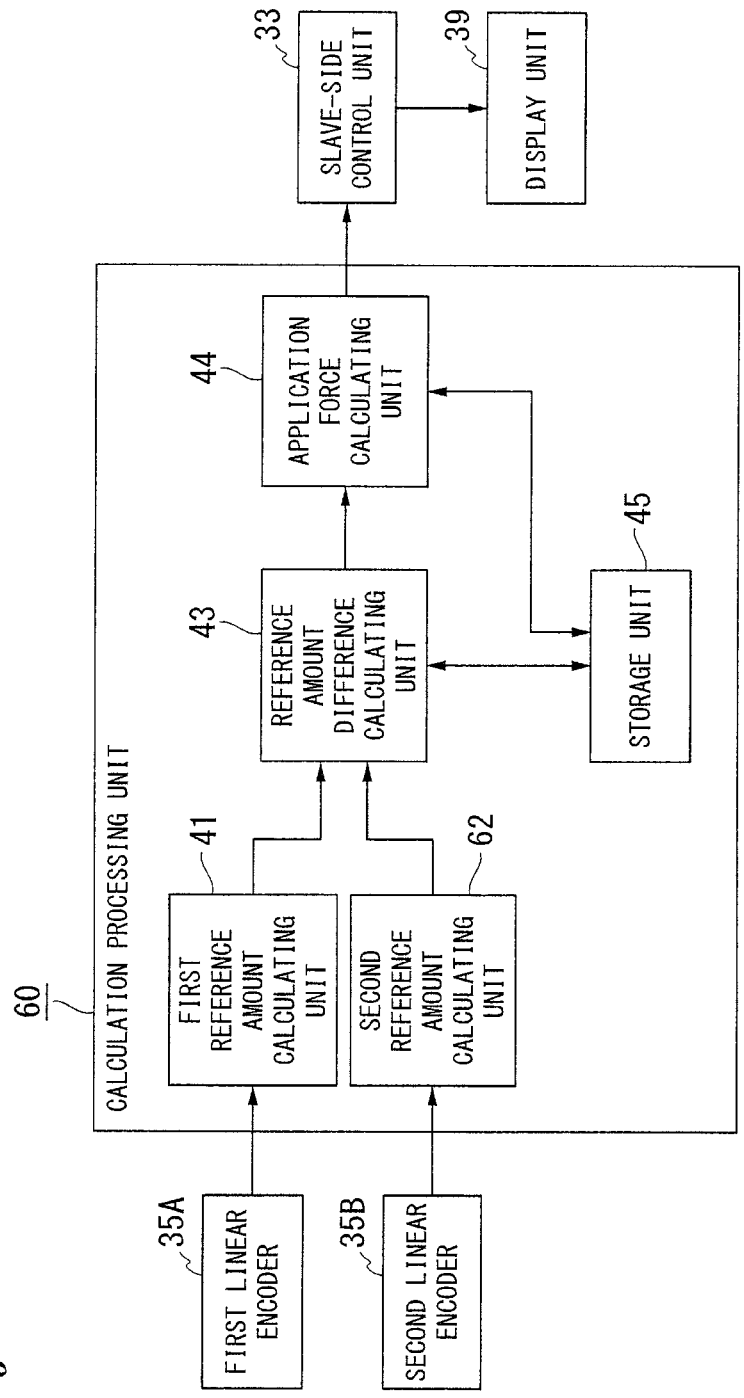
FIG. 6 is a functional block diagram illustrating a functional configuration of a calculation processing unit of the surgical instrument device according to the second embodiment of the present invention.

Next, a surgical instrument device according to a second embodiment will be described. FIG. 5 is a schematic cross-sectional view illustrating a configuration when a surgical instrument portion of a surgical instrument device according to a second embodiment of the present invention is detached. FIG. 6 is a functional block diagram illustrating a functional configuration of a calculation processing unit of the surgical instrument device according to the second embodiment of the present invention.

As shown in FIG. 5, the surgical instrument device 1B of the embodiment includes a first linear encoder 35A (first displacement detecting unit) and a second linear encoder 35B (second displacement detecting unit) inside the slave arm 31 of the surgical instrument device 1 of the first embodiment instead of the linear encoder 35 of the first embodiment. Furthermore, the surgical instrument device 1B of the embodiment includes a calculation processing unit 60 instead of the calculation processing unit 40 of the first embodiment. However, in the embodiment, the encoder 38 is electrically connected to only the slave-side control unit 33. Further, the surgical instrument device 1B may be appropriately used in the surgical operation assisting system 100 instead of the surgical instrument device 1 of the first embodiment. Hereinafter, differences from the first embodiment will be mainly described.

The first linear encoder 35A has the same configuration as the linear encoder 35 of the first embodiment, is provided at the same position, and detects the displacement of the point $P_1$ in the same way.

The second linear encoder 35B has the same configuration as the linear encoder 35 of the first embodiment. For this reason, the second linear encoder 35B has the detection position $Q_4$ corresponding to the detection position $Q_1$ of the linear encoder 35A, and is provided at a position at which the displacement of the point $P_4$ which is away from the point $P_1$ by the distance L toward the proximal end side on the driving rod 34 in a no-load state. The first linear encoder 35A and the second linear encoder 35B are each electrically connected to the calculation processing unit 60.

As shown in FIG. 6, the calculation processing unit 60 includes a second reference amount calculating unit 62 instead of the second reference amount calculating unit 42 of the calculation processing unit 40 of the first embodiment. The second reference amount calculating unit 62 has the same configuration as the first reference amount calculating unit 41 of the first embodiment. The second reference amount calculating unit 62 is electrically connected to the second linear encoder 35B, detects the displacement of the proximal end side point $P_4$ of two points away from each other in the axial direction on the driving rod 34 from the output of the second linear encoder 35B, and transmits the displacement as the displacement $\Delta X_2$ to the reference amount difference calculating unit 43.

Furthermore, in the storage unit 45 of the embodiment, corresponding to the output signal of the encoder 38 not being used for the calculation of the force F and the second linear encoder 35B detecting the displacement of the point $P_4$, data representing a correspondence relation between the rotation angle of the encoder 38 and the movement position of the point $P_2$ using the ball screw 36a is deleted, the displacement of the point $P_4$ in a no-load state is stored as the reference displacement $\Delta X_{02}$ in a no-load state, and the distance between the points $P_1$ and $P_4$ is stored as the distance L in a no-load state.

According to the configuration of the embodiment, it is possible to measure a change in distance between two points $P_1$ and $P_4$ on the driving rod 34 using the first linear encoder 35A and the second linear encoder 35B. For this reason, it is possible to calculate the force F acting on the driving rod 34 by the calculation processing unit 60 in the same way as the first embodiment.

Further, according to the embodiment, the displacement of the proximal end side point $P_4$ is detected by the second linear encoder 35B having the same configuration as that of the distal end side point $P_1$. For this reason, the second reference amount calculating unit 62 may not perform a calculation in which the rotation angle of the encoder 38 is converted into the movement amount of the linear driving block 36b. For this reason, a calculation for computing the displacement of the second reference amount calculating unit 62 is simplified. Further, since the same configuration as that of the first reference amount calculating unit 41 may be adopted, the configuration of the calculation processing unit 60 is simplified.

Further, the displacement of the point $P_4$ does not include a measurement error caused by the mechanical error of the linear driving mechanism 36. For this reason, even when there is a movement error of the linear driving mechanism 36, it is possible to highly precisely measure the displacement of the point $P_4$.

Further, the detection sensitivity of the force F may be easily changed by appropriately setting a gap between the points $P_1$ and $P_4$.

In the embodiment, the first linear encoder 35A and the second linear encoder 35B respectively constitute the first displacement detecting unit and the second displacement detecting unit. Further, the first linear encoder 35A, the second linear encoder 35B, the first reference amount calculating unit 41, the second reference amount calculating unit 62, and the reference amount difference calculating unit 43 constitute the distance change detecting unit which detects a change in distance $\Delta L$ between two points $P_1$ and $P_4$ away from each other in the axial direction on the driving rod 34 based on the distance L when no load is applied to the surgical instrument 32.

[Second Modified Example]

Figure 7:
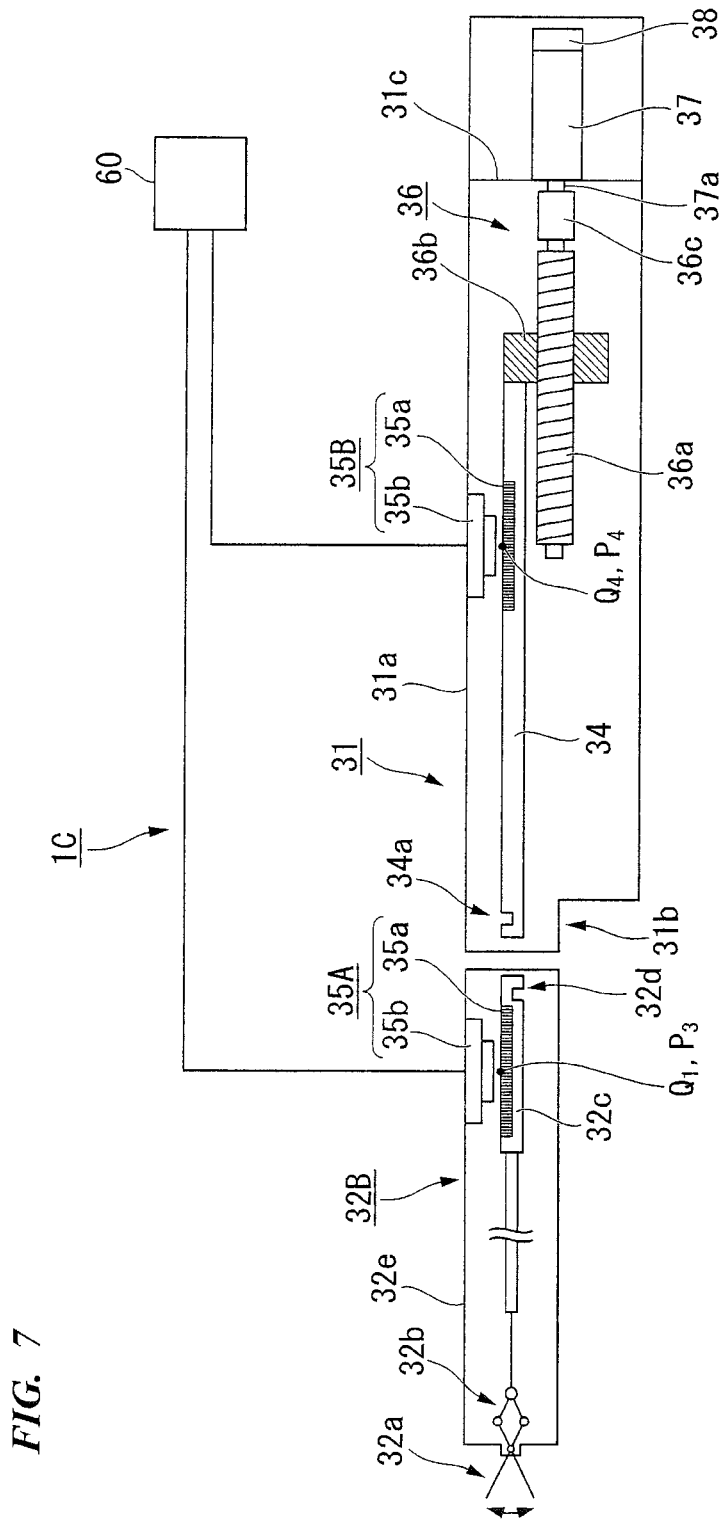
FIG. 7 is a schematic cross-sectional view illustrating a configuration when a surgical instrument portion of a surgical instrument device according to a modified example of the second embodiment of the present invention (second modified example) is detached.

Next, a modified example (second modified example) of the embodiment will be described. FIG. 7 is a schematic cross-sectional view illustrating a configuration when a surgical instrument portion of a surgical instrument device according to a modified example of the second embodiment (second modified example) of the present invention is detached.

As shown in FIG. 7, a surgical instrument device 1C of the modified example includes a surgical instrument 32B (surgical instrument portion) instead of the surgical instrument 32 of the surgical instrument device 1B of the second embodiment. Furthermore, the surgical instrument device 1C of the modified example does not include the first linear encoder 35A which is provided inside the slave arm 31 of the second embodiment. Further, the surgical instrument device 1C may be used in the surgical operation assisting system 100 instead of the surgical instrument device 1 of the first embodiment. Hereinafter, differences from the second embodiment will be mainly described.

The surgical operation tool 32B includes the first linear encoder 35A of the second embodiment instead of the linear encoder 35 of the surgical instrument 32A of the first modified example of the first embodiment.

According to the configuration of the modified example, it is possible to measure a change in distance between two points $P_3$ and $P_4$ on the shaft-like member when the driven portion 32c and the driving rod 34 are connected to each other by the first linear encoder 35A and the second linear encoder 35B. For this reason, it is possible to calculate the force F acting on the driven portion 32c and the driving rod 34 in the same way as the second embodiment. However, in the modified example, since the displacement of the point $P_3$ is measured instead of the displacement of the point $P_1$, the distance L in a no-load state or the displacement of the point $P_3$ in a no-load state change according to the position of the point $P_3$.

According to the modified example, it is possible to set a distance between two points used for the measurement of a change in distance long compared to the second embodiment. The modified example corresponds to an example in which the encoder 38 is replaced by the second linear encoder 35B in the second displacement detecting unit in the first modified example of the first embodiment.

[Third Modified Example]

Figure 8:
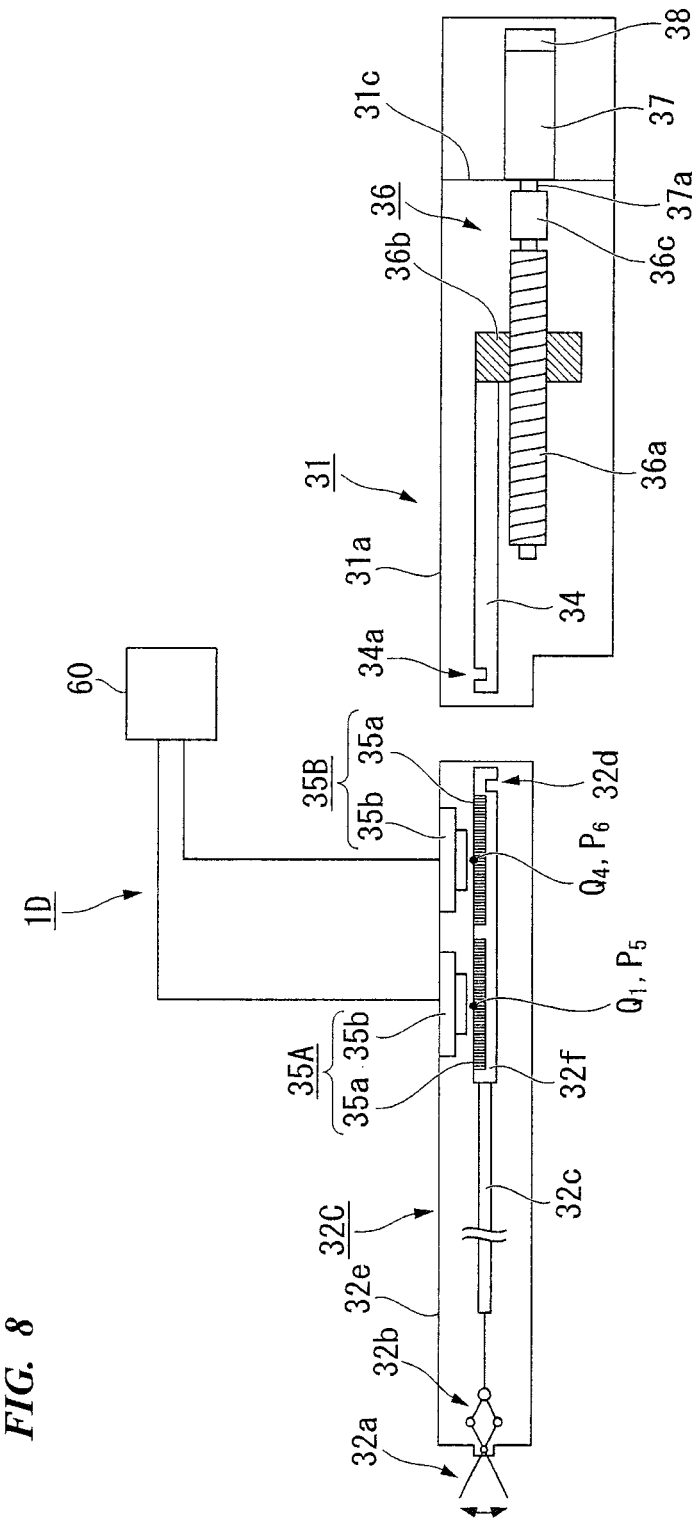
FIG. 8 is a schematic cross-sectional view illustrating a configuration when a surgical instrument portion of a surgical instrument device according to another modified example of the second embodiment of the present invention (third modified example) is detached.

Next, another modified example of the embodiment (third modified example) will be described. FIG. 8 is a schematic cross-sectional view illustrating a configuration when a surgical instrument portion of a surgical instrument device according to another modified example of the second embodiment of the present invention (third modified example) is detached.

As shown in FIG. 8, a surgical instrument device 1D of the modified example includes a surgical instrument 32C (surgical instrument portion) instead of the surgical instrument 32 of the surgical instrument device 1B of the second embodiment. Furthermore, in the surgical instrument device 1D of the modified example, the second linear encoder 35B which is provided inside the slave arm 31 of the second embodiment is not provided. Further, the surgical instrument device 1D may be used in the surgical operation assisting system 100 instead of the surgical instrument device 1 of the first embodiment. Hereinafter, differences from the second embodiment will be mainly described.

The surgical instrument 32C does not include the connection portion 32d of the driven portion 32c of the surgical instrument 32 of the second embodiment, and includes a distal end side driving rod portion 32f (distal end side force transmitting member) which is provided at the proximal end side of the driven portion 32c so that the shape of the cross-section perpendicular to the axis is the same as that of the driving rod 34 and the same material is used. Further, the proximal end of the distal end side driving rod portion 32f is provided with the connection portion 32d. Furthermore, the surgical operation tool 32C includes the first linear encoder 35A and the second linear encoder 35B so as to measure the displacements of two points $P_5$ and $P_6$ at the distal end side and the proximal end side of the distal end side driving rod portion 32f. That is, the scale portion 35a of the first linear encoder 35A and the scale portion 35a of the second linear encoder 35B are fixed to the distal end side driving rod portion 32f from the distal end side, and the respective detection portions 35b are provided in the inner peripheral surface of the surgical instrument housing 32e at the position facing the scale portions.

Furthermore, the distance between the detection position $Q_1$ of the first linear encoder 35A and the detection position $Q_4$ of the second linear encoder 35B may be set to an appropriate distance according to the measurement precision of the force F.

According to the configuration of the modified example, it is possible to measure a change in distance between two points $P_5$ and $P_6$ on the distal end side driving rod portion 32f corresponding to the respective detection positions $Q_1$ and $Q_4$ using the first linear encoder 35A and the second linear encoder 35B. For this reason, it is possible to calculate the force F acting on the distal end side driving rod portion 32f in the same way as the second embodiment. However, in the modified example, since the displacements of the points $P_5$ and $P_6$ are measured instead of the displacements of the points $P_1$ and $P_4$, the distance L in a no-load state or the displacements of the points $P_5$ and $P_6$ in a no-load state are changed according to the positions of the points $P_5$ and $P_6$.

According to the modified example, since the distance change detecting unit may be provided only in a side of the surgical operation tool 32C, a general configuration may be adopted as the configuration of the slave arm 31. Further, since the force may be calculated by detecting a change in distance near the gripping portion 32a, a detection precision of the force may be improved.

In the modified example, the distal end side driving rod portion 32f and the driving rod 34 respectively constitute the distal end side force transmitting member and the proximal end side force transmitting member, and the first displacement detecting unit and the second displacement detecting unit detect a change in distance between two points on the distal end side force transmitting member.

[Third Embodiment]

Figure 9:
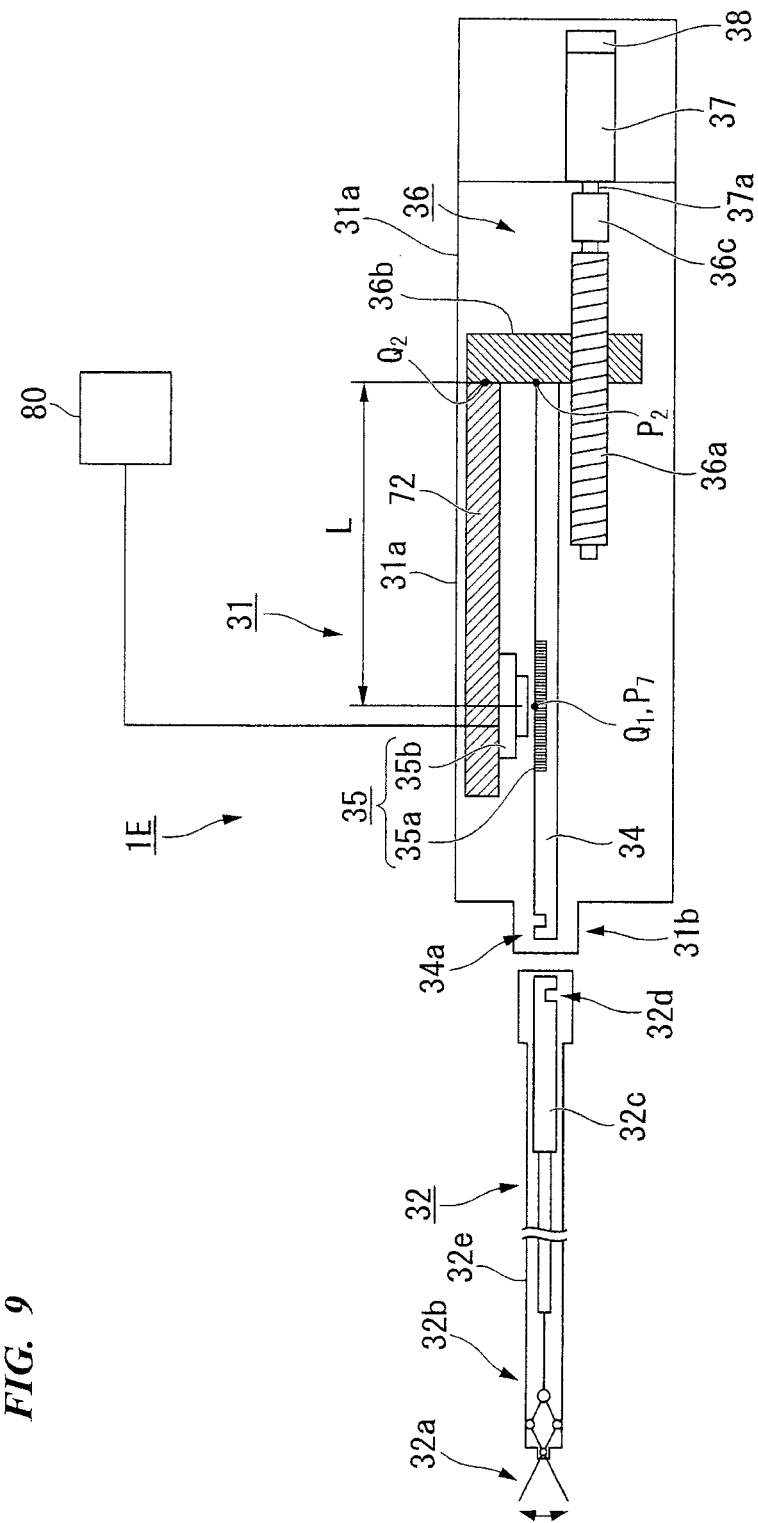
FIG. 9 is a schematic cross-sectional view illustrating a configuration when a surgical instrument portion of a surgical instrument device according to a third embodiment of the present invention is detached.
Figure 10:
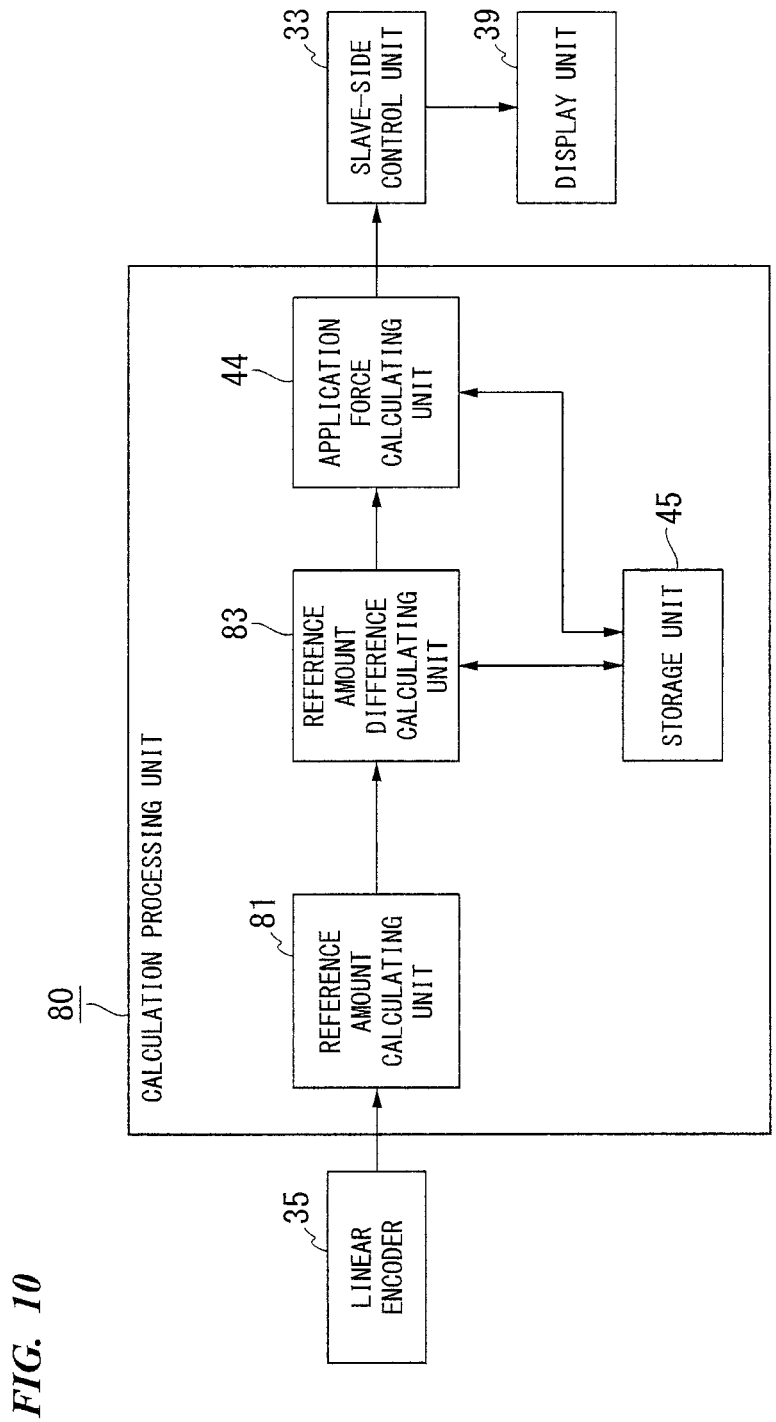
FIG. 10 is a functional block diagram illustrating a functional configuration of a calculation processing unit of the surgical instrument device according to the third embodiment of the present invention.

Next, a surgical instrument device according to a third embodiment will be described. FIG. 9 is a schematic cross-sectional view illustrating a configuration when a surgical instrument portion of a surgical instrument device according to a third embodiment of the present invention is detached. FIG. 10 is a functional block diagram illustrating a functional configuration of a calculation processing unit of the surgical instrument device according to the third embodiment of the present invention.

As shown in FIG. 9, a surgical instrument device 1E of the embodiment includes a reference member 72 (displacement detecting unit holding member) in the surgical instrument device 1 of the first embodiment, and includes a calculation processing unit 80 instead of the calculation processing unit 40. However, in the embodiment, the encoder 38 is electrically connected to only the slave-side control unit 33. Further, the surgical instrument device 1E may be appropriately used in the surgical operation assisting system 100 instead of the surgical instrument device 1 of the first embodiment.

Hereinafter, differences from the first embodiment will be mainly described.

The reference member 72 is a reference distance defining member which defines the distance L in a no-load state when measuring a change in distance between two points on the driving rod 34. In the embodiment, the proximal end surface $Q_2$ of the reference member 72 is fixed to the side surface contact with the point $P_2$ in the linear driving block 36b of the linear driving mechanism 36. The reference member 72 is formed from a thin and long block-shaped member which is provided at the side portion of the driving rod 34 so as to extend in parallel to the driving rod 34. The material of the reference member 72 is not particularly limited as long as the axial length is stably maintained even in the event of the environmental temperature, the external force in use, the vibration, or the like. For example, metal, ceramics, or the like having a small linear expansion coefficient may be adopted.

At the distal end side of the reference member 72, the detection portion 35b of the linear encoder 35 is fixed to the side surface facing the driving rod 34 at the position of the distance L from the proximal end surface $Q_2$. Here, the position of the detection portion 35b indicates a position at which the distance between the detection position $Q_1$ of the detection portion 35b and the proximal end surface $Q_2$ becomes L. Further, the scale portion 35a of the linear encoder 35 is fixed to the side surface of the driving rod 34 at a position facing the detection portion 35b.

In the scale portion 35a, in the embodiment, the point positioned at the detection position $Q_1$ when no load is applied to the surgical instrument 32 is the point $P_7$, and the distance between the points $P_7$ and $P_2$ becomes the distance in the above-described equation (4).

As shown in FIG. 10, the calculation processing unit 80 does not include the second reference amount calculating unit 42 of the calculation processing unit 40 of the first embodiment, and includes a reference amount calculating unit 81 and a reference amount difference calculating unit 83 instead of the first reference amount calculating unit 41 and the reference amount difference calculating unit 43.

The reference amount calculating unit 81 is electrically connected to the linear encoder 35, detects the displacement of the driving rod 34 at the detection position $Q_1$ of the detection portion 35b positioned at the distal end side on the driving rod 34 based on the output of the linear encoder 35, and transmits the displacement as the displacement $\Delta X_1$ to the reference amount difference calculating unit 83. As described in the first embodiment, since the displacement $\Delta X_1$ is common to the respective points on the scale portion 35a, it represents the displacement of the point $P_7$.

The reference amount difference calculating unit 83 calculates the difference $\Delta L$ between the displacement $\Delta X_1$ transmitted from the reference amount calculating unit 81 and the displacement $\Delta X_0$ of the point $P_7$ stored in advance in the storage unit 45 according to the following equation (5).

The difference $\Delta L$ calculated in the reference amount difference calculating unit 83 is transmitted to the application force calculating unit 44.

$$\Delta L = \Delta X_1 - \Delta X_0 \qquad (5)$$

The distance between the points $P_7$ and $P_2$ in the axial direction is defined by the position of the detection portion 35b in the reference member 72, and in the embodiment, is equal to the distance L. For this reason, the difference $\Delta L$ indicates a change in distance from the distance L when a load is generated in the surgical instrument 32.

When the surgical instrument 32 and the slave arm 31 are connected to each other and a current is supplied to the surgical instrument device 1E, the surgical instrument device 1E is initialized by the slave-side control unit 33. At this time, the origin of the linear encoder 35 is reset, and in the following operations, the position is set to a position of $\Delta X_1 = 0$. Thus, when no load is applied to the surgical instrument 32 in the initialization state, the origin is used as the reference of a position in a no-load state, so that $\Delta X_0 = 0$.

However, as with the first embodiment, there are cases in which a load needs to be applied to the surgical instrument 32 in the initialization state. In this case, the origin in the initialization state may not be set to a position in a no-load state. For this reason, in the embodiment, the driving states of the surgical instrument 32 in an initialization state and a no-load state are defined for each surgical instrument 32, the displacement $\Delta X_0$ in a no-load state measured from the origin in an initialization state is measured in advance, and then the displacement is stored in the storage unit 45.

The application force calculating unit 44 calculates the force F using the above-described equation (4) as with the first embodiment. However, in the embodiment, $\Delta L$ used in the above-described equation (4) is a value which is calculated in the above-described equation (5) and is transmitted from the reference amount difference calculating unit 83. Further, the distance L in a no-load state in the above-described equation (4) indicates a distance between the points $P_7$ and $P_2$ determined based on the attachment position of the detection portion 35b in the reference member 72. Further, S in the above-described equation (4) indicates the cross-sectional area of the cross-section perpendicular to the axis between the points $P_7$ and $P_2$ of the driving rod 34.

For this reason, the storage unit 45 of the embodiment does not store data representing a correspondence relation between the rotation angle of the encoder 38 and the movement position of the point $P_2$ using the ball screw 36a. Furthermore, the storage unit 45 of the embodiment stores the displacement $\Delta X_0$ in a no-load state instead of the reference displacements $\Delta X_{01}$ and $\Delta X_{02}$, and stores the distance between the points $P_7$ and $P_2$ as the distance L in a no-load state.

According to the configuration of the embodiment, the linear encoder 35 is fixed to the reference member 72 provided with the proximal end surface $Q_2$ at the same position as that of the point $P_2$ of the proximal end of the driving rod 34. For this reason, it is possible to measure a change in distance between the points $P_7$ and $P_2$ when no load is applied to the surgical instrument 32, and calculate the force F acting on the driving rod 34 by the calculation processing unit 80 in the same way as the first embodiment.

In the embodiment, since the reference member 72 is used, a change in distance between two points may be measured by only one linear encoder 35, and hence the configuration of the calculation processing unit 80 is simplified. For this reason, it is possible to obtain a surgical instrument device with a simple and low-cost configuration as a whole.

In the embodiment, the linear encoder 35, the reference amount calculating unit 81, and the reference amount difference calculating unit 83 constitute the distance change detecting unit which detects a change in distance $\Delta L$ between two points $P_7$ and $P_2$ away from each other in the axial direction on the driving rod 34 based on the distance L when no load is applied to the surgical instrument 32. Further, the linear encoder 35 constitutes the displacement detecting unit which detects the displacement of one point $P_7$ of two points $P_7$ and $P_2$ away from each other in the axial direction on the driving rod 34.

Further, the reference member 72 constitutes the displacement detecting unit holding member which is fixed to the other point $P_2$ of two points $P_7$ and $P_2$ away from each other in the axial direction on the driving rod 34, extends in the axial direction of the driving rod 34, and holds the displacement detecting unit at the predetermined distance L from the other point $P_2$.

[Fourth Embodiment]

Figure 11:
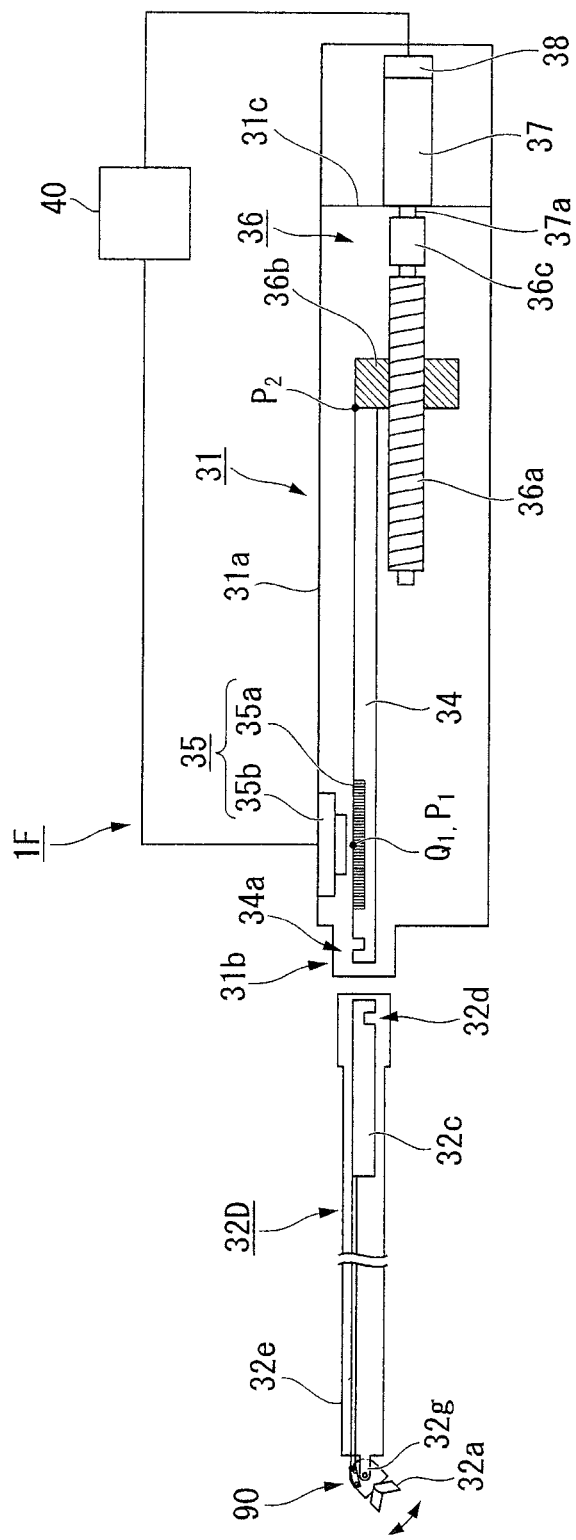
FIG. 11 is a schematic cross-sectional view illustrating a configuration when a surgical instrument portion of a surgical instrument device according to a fourth embodiment of the present invention is detached.
Figure 12A:
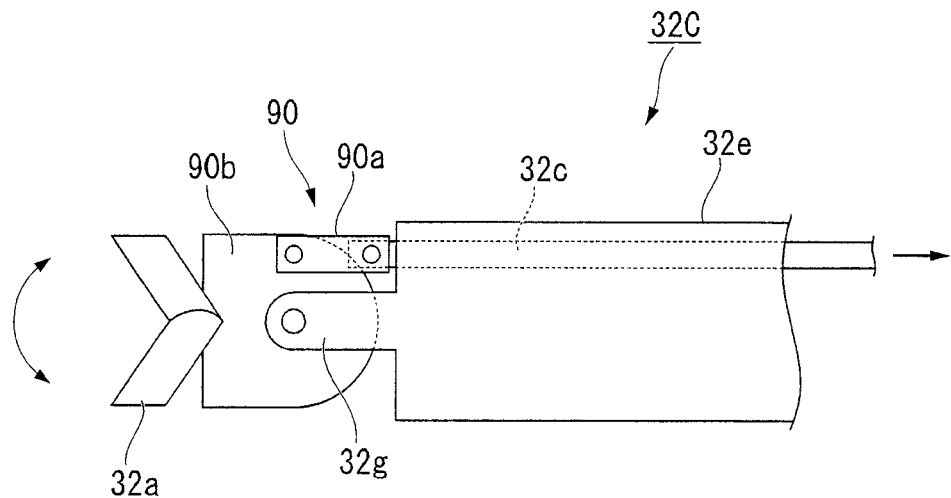
FIG. 12A is a schematic explanatory diagram of an operation of the surgical instrument portion according to the fourth embodiment of the present invention.
Figure 12B:
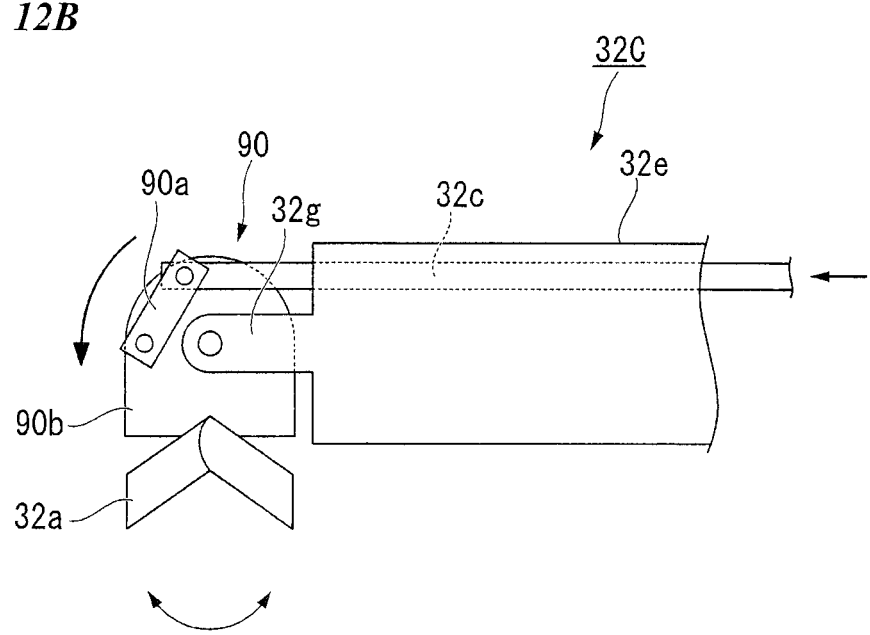
FIG. 12B is a schematic explanatory diagram of an operation of the surgical instrument portion according to the fourth embodiment of the present invention.

Next, a surgical instrument device according to a fourth embodiment will be described. FIG. 11 is a schematic cross-sectional view illustrating a configuration when a surgical instrument portion of a surgical instrument device according to a fourth embodiment of the present invention is detached. FIGS. 12A and 12B are schematic diagrams illustrating an operation of the surgical instrument portion according to the fourth embodiment of the present invention.

As shown in FIGS. 11, 12A, and 12B, a surgical instrument device 1F of the embodiment includes a surgical instrument 32D (surgical instrument portion) instead of the surgical instrument 32 of the surgical instrument device 1 of the first embodiment. Further, the surgical instrument device 1F may be appropriately used in the surgical operation assisting system 100 instead of the surgical instrument device 1 of the first embodiment. Hereinafter, differences from the first embodiment will be mainly described.

The surgical operation tool 32D includes a joint 90 which turnably supports the gripping portion 32a of the surgical instrument 32 of the first embodiment. The driving rod 34, the linear driving mechanism 36, and the motor 37 are used to rotate the joint 90.

The joint 90 includes a joint body 90b which is rotatably provided in the rotary support portion 32g provided in the distal end of the surgical instrument housing 32e and a driving rod 90a which rotates the joint body 90b by applying a moment about the rotary support axis of the rotary support portion 32g to the joint body 90b. One end of the driving rod 90a is rotatably connected to the joint body 90b, and the other end of the driving rod 90a is rotatably connected to the distal end of the driven portion 32c.

Further, the driving mechanism of the gripping portion 32a is omitted in the drawings, but the gripping portion 32a is opened and closed by a driving mechanism different from such a driving mechanism which drives the joint 90. For example, the gripping portion 32a may be driven by the same configuration as that of the first embodiment. Further, when there is no need to detect the force acting on the gripping portion 32a, for example, wire driving or the like may be used only to open and close the gripping portion 32a.

With the above-described configuration, the surgical instrument 32D is connected to the slave arm 31. Then, when the motor 37 drives the driving rod 34 so that the driving rod 34 advances and retracts, the joint 90 can be rotated.

Further, for example, when the driving rod 34 retracts toward the proximal end side, as shown in FIG. 12A, the joint body 90b turns, and the gripping portion 32a faces the distal end of the surgical operation tool 32D. In this state, the gripped object can be gripped.

Further, when the driving rod 34 advances toward the distal end side, the moment of the force is applied from the driving rod 90a to the joint body 90b through the driven portion 32c. Then, the gripping portion 32a is directed toward a side surface direction intersecting the axial direction, and in this state, the gripped object can be gripped.

Further, for example, in a case in which the treated portion is gripped as the gripped object, for example, when the joint 90 is rotated, the treated portion is twisted, so that a moment acts on the joint body 90b against the motion of the joint 90. The moment is transmitted as a force which advances and retracts the driven portion 32c through the driving rod 90a, and the force acts on the distal end portion of the driving rod 34 through the connection portion 32d. As a result, the force F acting on the driving rod 34 is detected in the same way as the first embodiment, and is displayed on the display unit 39. For this reason, the operator $O_p$ may evaluate the magnitude of the resistance force against the joint 90 by viewing the magnitude of the force F, and can adjust the manipulation.

[Fourth Modified Example]

Figure 13:
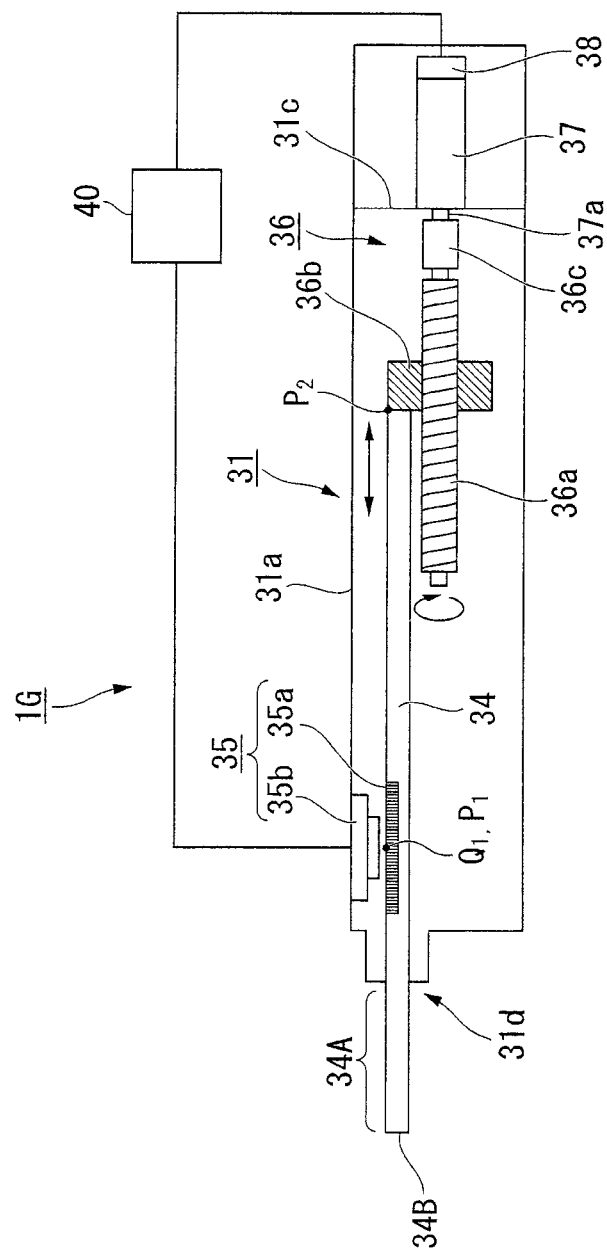
FIG. 13 is a schematic cross-sectional view illustrating a configuration of a surgical instrument device according to a modified example of the fourth embodiment (fourth modified example) of the present invention.

Next, a surgical instrument device according to a modified example of the embodiment (fourth modified example) will be described. FIG. 13 is a schematic cross-sectional view illustrating a configuration of a surgical instrument device according to a modified example of the fourth embodiment of the present invention (fourth modified example).

As shown in FIG. 13, a surgical instrument device 1G of the modified example is a modified example of the surgical instrument portion of the surgical instrument device 1F of the fourth embodiment. The surgical instrument device 1G of the modified example does not include the surgical instrument 32D of the surgical instrument device 1F, and includes an opening portion 31d instead of the fitting portion 31b of the arm housing 31a. Further, the distal end of the driving rod 34 is provided with the surgical instrument portion 34A instead of the connecting portion 34a. Further, the surgical instrument device 1G may be used in the surgical operation assisting system 100 instead of the surgical instrument device 1 of the first embodiment. Hereinafter, differences from the fourth embodiment will be mainly described.

The surgical instrument portion 34A is a bar-like member which protrudes from the inside of the arm housing 31a toward the outside of the arm housing 31a through the opening portion 31d. The distal end portion of the surgical instrument portion 34A is provided with, for example, a pressing surface 34B which is used to press the treated portion or pressurize the treated portion so as to examine the hardness or the like of the affected portion. The surgical instrument portion 34A may be provided so as to be attachable to and detachable from the distal end of the driving rod 34, but in the modified example, is integrated with the driving rod 34.

With the above-described configuration, a surgical instrument device 1G of the modified example may perform a pressing operation while evaluating the pressure and the hardness of the treated portion or the like related to the pressure by the force F when the pressing surface 34B of the surgical instrument portion 34A is pressed against the treated portion or the like.

The modified example corresponds to an example in which the surgical instrument portion is not attachable to and detachable from the surgical instrument device body. Further, the modified example corresponds to an example in which the surgical instrument portion does not include the movable portion.

[Fifth Embodiment]

Figure 14A:
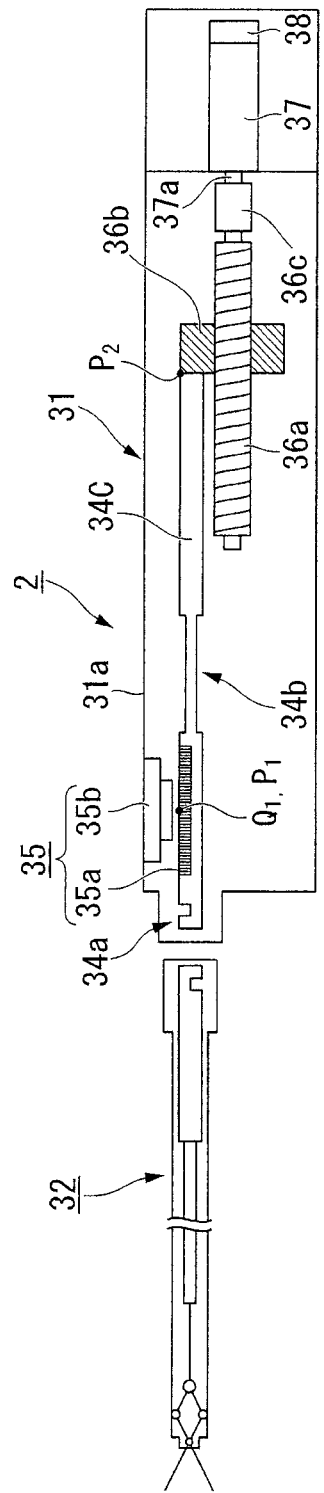
FIG. 14A is a schematic cross-sectional view illustrating a configuration when a surgical instrument portion of a surgical instrument device according to a fifth embodiment of the present invention is detached.

Next, a surgical instrument device according to a fifth embodiment will be described. FIG. 14A is a schematic cross-sectional view illustrating a configuration when a surgical instrument portion of a surgical instrument device according to a fifth embodiment of the present invention is detached.

As shown in FIG. 14A, the surgical instrument device 2 of the embodiment includes a driving rod 34C (force transmitting member) instead of the driving rod 34 of the surgical instrument device 1 of the first embodiment. Furthermore, in FIG. 14A, the calculation processing unit 40 is omitted for simplicity of drawings. Further, the surgical instrument device 2 may be appropriately used in the surgical operation assisting system 100 instead of the surgical instrument device 1 of the first embodiment. Hereinafter, differences from the first embodiment will be mainly described.

The driving rod 34C is formed as a bar-like member of which the size of the cross-section perpendicular to the axis is not uniform in the axial direction. In the embodiment, a small diameter portion 34b (distance change amplifying portion) of which the cross-sectional area of the cross-section perpendicular to the axis is smaller than those of both end portions is provided between the points $P_1$ and $P_2$ of the driving rod 34 of the first embodiment.

With the above-described configuration, when a force acts on both ends of the driving rod 34C, the deformation of the small diameter portion 34b of which the cross-sectional area of the cross-section perpendicular to the axis is small relatively increases. For this reason, it is possible to improve the detection sensitivity of the force F compared to the driving rod 34. That is, even when the driving rod 34C and the driving rod 34 have the same length, a change in distance between two points $P_1$ and $P_2$ with respect to the force acting on the driving rod 34C further increases. For this reason, since the entire length of the driving rod 34C may be shortened when detecting the same force, a compact surgical instrument device is obtained.

[Fifth Modified Example]

Figure 14B:
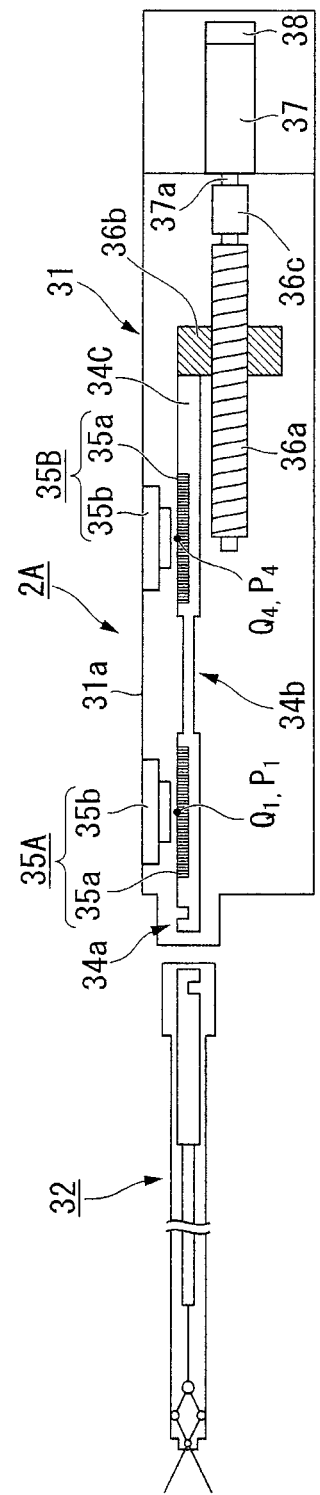
FIG. 14B is a schematic cross-sectional view illustrating a configuration when a surgical instrument portion of a surgical instrument device according to a modified example of the fifth embodiment of the present invention (fifth modified example) is detached.

Next, a surgical instrument device according to a modified example of the fifth embodiment (fifth modified example) will be described. FIG. 14B is a schematic cross-sectional view illustrating a configuration when a surgical instrument portion of a surgical instrument device according to a modified example of the fifth embodiment of the present invention (fifth modified example) is detached.

As shown in FIG. 14B, a surgical instrument device 2A of the modified example is a device which uses the driving rod 34C of the fifth embodiment instead of the driving rod 34 of the surgical instrument device 1B of the second embodiment. As well, in FIG. 14B, the calculation processing unit 60 is omitted for simplicity of drawings Further, the surgical instrument device 2A may be appropriately used in the surgical operation assisting system 100 instead of the surgical instrument device 1 of the first embodiment.

Even in the surgical instrument device 2A, a change in distance between two points $P_1$ and $P_4$ further increases compared to the surgical instrument device 1B of the second embodiment due to the action of the small diameter portion 34b of the driving rod 34C, and hence a compact surgical instrument device is obtained.

[Sixth Modified Example]

Figure 14C:
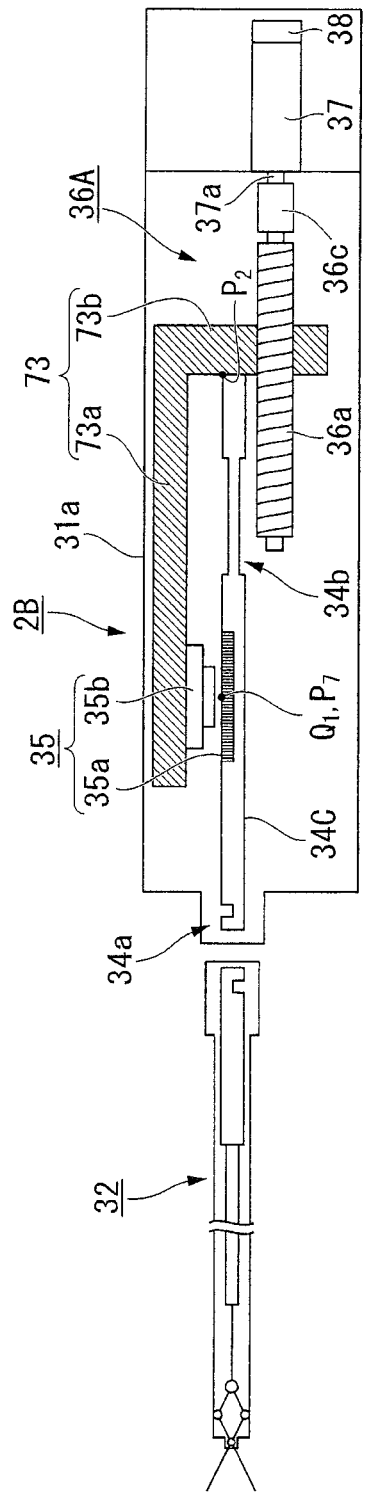
FIG. 14C is a schematic cross-sectional view illustrating a configuration when a surgical instrument portion of a surgical instrument device according to another modified example of the fifth embodiment of the present invention (sixth modified example) is detached.

Next, a surgical instrument device according to another modified example of the fifth embodiment (sixth modified example) will be described. FIG. 14C is a schematic cross-sectional view illustrating a configuration when a surgical instrument portion of a surgical instrument device according to another modified example of the fifth embodiment of the present invention (sixth modified example) is detached.

As shown in FIG. 14C, a surgical instrument device 2B of the modified example is a device which uses the driving rod 34C of the fifth embodiment instead of the driving rod 34 of the surgical instrument device 1E of the third embodiment. Further, the surgical instrument device 2B includes a linear driving mechanism 36A instead of the linear driving mechanism 36 of the surgical instrument device 1E of the third embodiment. In the linear driving mechanism 36A, the configuration of the L-shaped block in which the reference member 72 of the surgical instrument device 1E is fixed to the linear driving block 36b is replaced by an L-shaped block 73 in which a reference portion 73a and a linear driving block portion 73b, which corresponds to each, are integrated with each other. Furthermore, in FIG. 14C, the calculation processing unit 80 is omitted for simplicity of drawings. Further, the surgical instrument device 2B may be appropriately used in the surgical operation assisting system 100 instead of the surgical instrument device 1 of the first embodiment.

In the surgical instrument device 2B, a change in distance between two points $P_7$ and $P_2$ further increases compared to the surgical instrument device 1E of the fifth embodiment by the action of the small diameter portion 34b of the driving rod 34C, and hence a compact surgical instrument device is obtained.

Furthermore, in the description above, a case has been described in which the linear encoders 35, 35A, and 35B are respectively used as the displacement detecting unit, the first displacement detecting unit, and the second displacement detecting unit. However, a displacement detector other than the linear encoder may be adopted. For example, as the displacement detector, a laser displacement gauge, a magnetic displacement gauge, and the like may be given.

Further, in the description above, a case has been described in which the linear encoder used in each displacement detecting unit is of an incremental type, but a linear encoder of an absolute value type may be adopted. In this case, since the position measurement on the scale can be performed, it is possible to measure the displacement at an arbitrary point on the scale. Thus, ΔL may be obtained by the difference between the displacements of two points.

Further, in the description above, a case has been described in which the surgical instrument device includes the driving unit, but the driving unit may not be provided. For example, in the fourth embodiment, the linear driving mechanism 36 and the motor 37 may not be provided, the proximal end portion of the driving rod 34 may be fixed to the proximal end side position of the arm housing 31a, and in the same way as the second embodiment, a change in distance between two points on the driving rod 34 may be detected by the first linear encoder 35A and the second linear encoder 35B. In this case, it is possible to detect the pressure when the slave arm 31 is advanced and retracted with respect to the treated portion by the articulated robot 30a or detect the reaction force from the treated portion or the like when the slave arm 31 is fixed.

Further, all components illustrated in the above-described embodiments may be appropriately combined or omitted without departing from the scope of the present invention. For example, in the respective embodiments and the respective modified examples in which the surgical instrument portion is attachable to and detachable from the surgical instrument device body, as in the fourth embodiment, the surgical instrument portion and the surgical instrument device body may be integrated with each other, one shaft-like member obtained by integrating the driven portion 32c and the driving rod 34 with each other may be inserted from the surgical instrument device body into the surgical instrument portion, and then the application force may be applied to the movable portion such as the gripping portion 32a or the like of the surgical instrument portion.

While preferred embodiments of the present invention have been described and illustrated above, it should be understood that these are exemplary of the present invention and are not to be considered as limiting. Additions, omissions, substitutions, and other modifications can be made without departing from the spirit or scope of the present invention. Accordingly, the present invention is not to be considered as being limited by the foregoing description, and is only limited by the scope of the appended claims.

What is claimed is:

1. A surgical device comprising:
   a surgical instrument;
   a device body configured to hold the surgical instrument;
   a force transmitting member formed in a shaft shape extending in an axial direction, wherein a first end portion of the force transmitting member in the axial direction is connected to the surgical instrument and a second end portion of the force transmitting member in the axial direction is supported by the device body, wherein the force transmitting member is configured to transmit a force between the surgical instrument and the device body;
   a distance change detector configured to detect a change in distance between two points away from each other in the axial direction on the force transmitting member based on a distance when no load is applied to the surgical instrument; and
   a processor configured to calculate a force applied from the surgical instrument or the device body to the force transmitting member based on the change in distance detected by the distance change detector,
   wherein the distance change detector comprises:
      a first displacement detector configured to detect a displacement of a distal end side point of the two points away from each other in the axial direction on the force transmitting member; and
      a second displacement detector configured to detect a displacement of a proximal end side point of the two points away from each other in the axial direction on the force transmitting member, and
   wherein the processor is configured to:
      convert the displacement of the distal end side point detected by the first displacement detector and the displacement of the proximal end side point detected by the second displacement detector into the displacements based on a position where no load is applied to the surgical instrument, and
      calculate the change in distance by calculating a difference between the displacement of the distal end side point and the displacement of the proximal end side point after the conversion.

2. The surgical device according to claim 1,
wherein the processor is configured to:
- control a storage to store a conversion equation for converting the change in distance into the force applied from the surgical instrument or the device body to the force transmitting member; and
- perform a calculation for converting the change in distance into the force applied from the surgical instrument or the device body to the force transmitting member using the conversion equation.

3. The surgical device according to claim 1,
wherein at least one of the first displacement detector and the second displacement detector is comprised of a linear encoder.

4. The surgical device according to claim 1,
wherein the device body comprises a driving mechanism configured to advance and retract the second end portion of the force transmitting member in the axial direction, and
wherein the force transmitting member is supported by the device body through the driving mechanism.

5. The surgical device according to claim 4,
wherein the second displacement detector comprises an encoder connected to the driving mechanism, wherein the encoder is configured to detect a driving amount of an advance and retract driving at the second end portion of the force transmitting member by the driving mechanism.

6. The surgical device according to claim 1,
wherein the surgical instrument is configured to be attachable to and detachable from the device body, and
wherein the force transmitting member comprises:
- a distal end side force transmitting member provided in the surgical instrument, wherein the distal end side force transmitting member comprises a first connection portion provided at a proximal end side thereof; and
- a proximal end side force transmitting member provided in the device body,
wherein the proximal end side force transmitting member comprises a second connection portion provided at a distal end side thereof so as to be connected to the first connection portion of the distal end side force transmitting member.

7. The surgical device according to claim 6,
wherein the first displacement detector is configured to detect a displacement of a point on the distal end side force transmitting member, and
wherein the second displacement detector is configured to detect a displacement of a point on the proximal end side force transmitting member.

* * * * *